(12) United States Patent
Balthes

(10) Patent No.: US 10,308,414 B2
(45) Date of Patent: Jun. 4, 2019

(54) METHOD AND SYSTEM FOR CALCULATING A SUITABILITY INDICATOR

(71) Applicant: Boehringer Ingelheim International GmbH, Ingelheim am Rhein (DE)

(72) Inventor: Eduard Balthes, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 180 days.

(21) Appl. No.: 15/308,505

(22) PCT Filed: May 5, 2015

(86) PCT No.: PCT/EP2015/000918
§ 371 (c)(1),
(2) Date: Dec. 6, 2016

(87) PCT Pub. No.: WO2015/169439
PCT Pub. Date: Nov. 12, 2015

(65) Prior Publication Data
US 2017/0247161 A1     Aug. 31, 2017

(30) Foreign Application Priority Data

May 5, 2014   (EP) .................................... 14001556
May 6, 2014   (EP) .................................... 14001580

(51) Int. Cl.
| | |
|---|---|
| *B65D 79/02* | (2006.01) |
| *A61J 1/03* | (2006.01) |
| *G01N 15/08* | (2006.01) |
| *G01N 33/15* | (2006.01) |
| *G01N 17/00* | (2006.01) |

(52) U.S. Cl.
CPC ................ *B65D 79/02* (2013.01); *A61J 1/03* (2013.01); *G01N 15/08* (2013.01); *G01N 17/00* (2013.01); *G01N 33/15* (2013.01)

(58) Field of Classification Search
CPC .. B65D 79/02; G01N 33/15; A61J 1/03; A61J 1/035
See application file for complete search history.

(56) References Cited

U.S. PATENT DOCUMENTS

2006/0201602 A1     9/2006  Nair

OTHER PUBLICATIONS

International Search Report for corresponding PCT Application No. PCT/EP2015/000918, 3 pages, dated Sep. 16, 2015.
Allinson J G et al: "The effects of packaging on the stability of a moisture sensitive compound" International Journal of Pharmaceutics, vol. 221, No. 1-2, pp. 49-56, Jun. 19, 2001.
Pfeiffer C et al: "Optimizing Food Packaging and Shelf Life" Food Technology, Institute of Food Technologists, Chicago, IL, US, vol. 53, No. 6, pp. 52-59, Jun. 30, 1999.
Remco Van Weeren et al"Determining drug stability and selecting packaging" URL:http://www.bilcare.comjpdf/BilcareOptima_pmpn_publication.pdf, pp. 70-75, Dec. 31, 2007.
Mahajan et al: "Development of user-friendly software for design of modified atmosphere packaging for fresh and fresh-cut produce" Innovative Food Science and Emerging Technologies, Elsevier, Amsterdam, NL, vo 1 • 8, No. 1, pp. 84-92, Feb. 12, 2007.

*Primary Examiner* — Christopher Adam Hixson
(74) *Attorney, Agent, or Firm* — Matthew B. Dernier, Esq.

(57) ABSTRACT

Methods and systems for calculating a suitability indicator which corresponds to a suitability of a packaging system for packaging a substance, where a stability indicator which corresponds to a stability of the substance or of a component of the substance is determined as a function of at least one ambient condition, preferably the relative humidity and/or temperature of the environment of the substance, and the suitability indicator is calculated with at least one parameter relating to the ambient condition and with the stability indicator of the substance.

23 Claims, 5 Drawing Sheets

METHOD AND SYSTEM FOR CALCULATING A SUITABILITY INDICATOR

Figure 1:
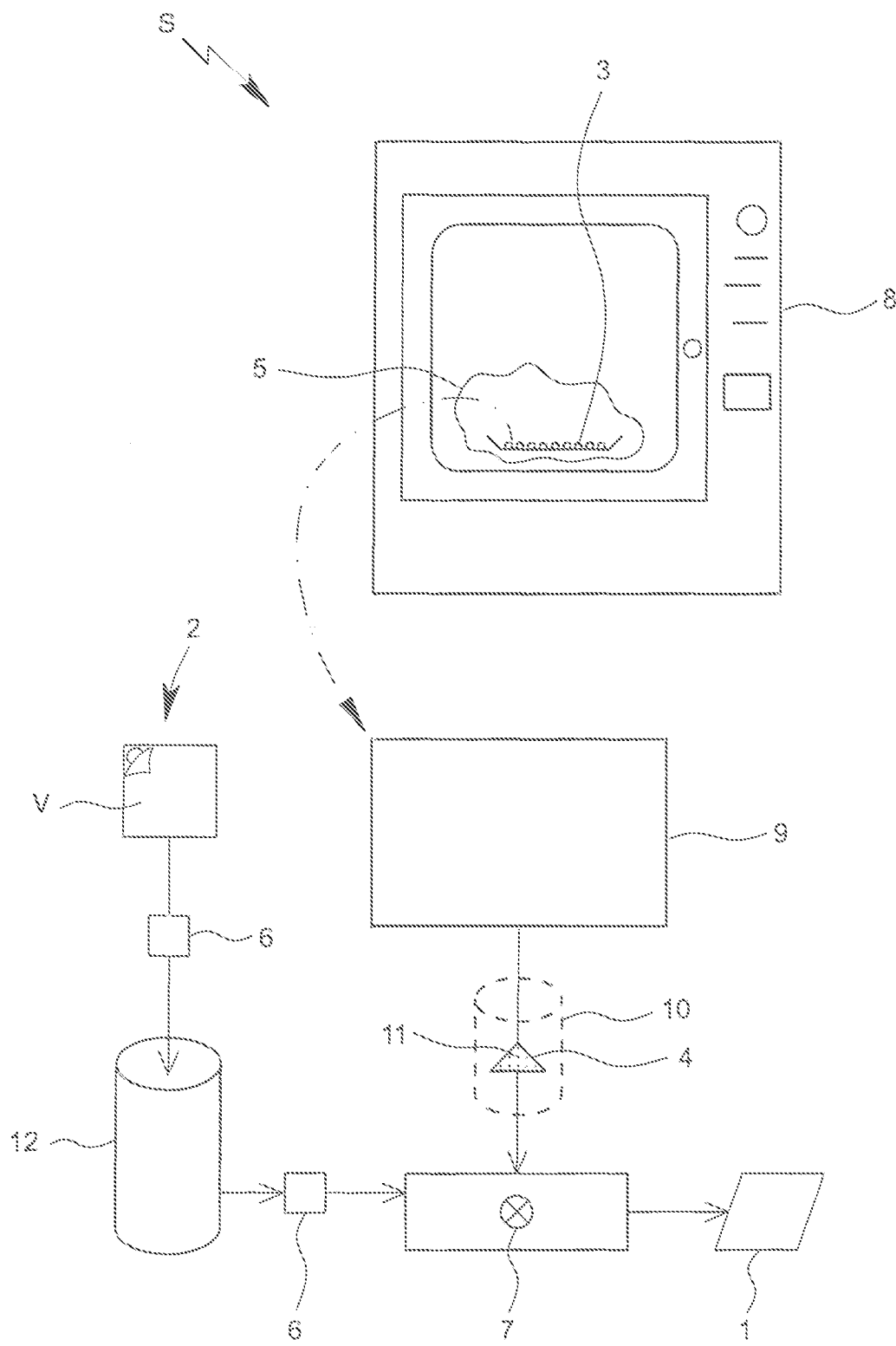

The present invention relates to a method and a system connected with the packaging of substances, preferably tablets or other medicaments, particularly for ensuring a long shelf life.

The present invention is hereinafter always described in connection with the packaging of substances by means of a packaging system. Preferably, the substance is a medicament. The medicament preferably comprises at least one active substance and/or an excipient. The medicament is preferably present as a solid, particularly in the form of a plurality of discrete units, in the form of a loose dry compacted material, in the form of tablets or in the form of capsules. However, the present invention is not restricted to the packaging of medicaments. The present invention may also be used, and advantageously used, for identifying suitable packaging systems for a different substance or for determining properties, particularly storage properties, of a different substance when packaged using a packaging system.

Therefore, the present invention is hereinafter generally described in connection with substances and packaging systems for them, even though the example of the packaging of medicaments, particularly tablets, is always in the foreground.

A packaging system in the sense of the present invention is or comprises a packaging, in particular. A packaging system preferably also comprises steps or means for packing the substance. The term "packaging system" may go beyond the packaging as such and takes into account, in particular, the materials enclosed together with the substance in the closure process, the development of heat, radiation or other influencing factors which may possibly have an effect on the substance.

Substances, particularly medicaments or tablets, are regularly subject to an ageing process. This may become evident from the fact that chemical quality parameters, for example, a concentration of active substance, a change in the concentration of active substance, dissolving, decomposition or the like and/or physical quality parameters such as, for example, properties connected with breaking force, disintegration or the like may change.

In order to determine the stability of a substance in the packaged state, packaging studies are conventionally carried out in which the substance, particularly the medicament, is exposed to different influencing factors in a primary package and in this way the suitability of a packaging for the substance in question is determined experimentally under specific external constraints. Thus, long-term tests are carried out in which the substance is packaged and the side of the package remote from the substance is exposed to certain climatic conditions or other constraints. However, it has been found that, because of the multiplicity of possible packaging systems and the immense work and the processes, some lasting several years, it may be very labor-intensive, expensive and tedious to determine a combination of substance and packaging system which is suitable for an individual case.

The aim of the present invention is therefore to provide a method and a system by means of which the determination of a packaging system can be improved or speeded up and/or made cheaper.

This aim is achieved by a method according to one or more disclosed embodiments. Advantageous further features are also disclosed.

It is proposed that a suitability indicator is calculated which corresponds to the suitability of a packaging system for packaging a substance.

The suitability indicator may, in particular, be or comprise: a development of an absolute or relative water content of the packaged substance over time, an absolute or relative water content of the packaged substance after a certain time, a degree of decomposition or degradation or the proportion of unwanted decomposition products in the packaged substance resulting from the change in the water content over time, the development of a level of decomposition or degradation or the proportion of unwanted decomposition products in the packaged substance resulting from the change in the water content over time, preferably in a particular climate or climatic conditions determined on the outside of the packaging or on the side of the packaging remote from the substance, an absorption curve, for example a sorption isotherm, of the substance packaged with the packaging system, particularly under pre-definable climatic ambient conditions, representing a water content or a water uptake of the substance over time, or a degradation pattern determined therefrom, particularly by calculation.

The suitability indicator may be associated with a packaging or a packaging system. The suitability indicator may be an allocation of specific packaging materials, amounts and/or forms of packaging, desiccants and/or excipients such as desiccants as part of the substance or inside the packaging or in the same atmosphere or the same volume formed by the packaging.

The suitability indicator may preferably be or comprise a Boolean value or one or more characteristics or parameters, particularly corresponding to materials, amounts and/or forms of packaging, of desiccants and/or excipients such as desiccants as part of the substance, optionally also corresponding to other process conditions such as temperature and ambient humidity in the manufacturing or packaging machine or the like.

In a departure from the previous method for testing different packaging systems by experiment, suitability here is determined by computation. This advantageously enables different packaging systems to be evaluated for their suitability for packaging the substance and to discard packaging systems, which are fundamentally unsuitable on this basis from the outset and/or select fundamentally well-suited packaging systems. Alternatively or additionally, more suitable packaging systems may be indicated, displayed or labeled. For this purpose, suitability indicators of different packaging systems may be compared with one another and/or with a threshold or target value. In this way, both the amount of work and the time spent determining and verifying the suitability of a packaging system for a substance can be improved.

According to an aspect of the present invention, which may also be implemented independently, a stability indicator is determined which corresponds to a stability of the substance or of a component of the substance. This is preferably carried out as a function of at least one ambient condition, particularly (relative) humidity and/or temperature and/or climate and/or (UV) radiation with a specific energy.

For example, the stability indicator comprises a value or parameter, which describes how an active substance comprising the substance breaks down into a toxic product or becomes mechanically instable as a function of the water content of the substance, the temperature and the time. Moreover, a maximum limit is preferably set, particularly as part or parameter of the stability indicator. This maximum limit then constitutes the threshold value, particularly a maximum absolute or relative quantity, of the decomposition product. Alternatively or additionally the maximum limit constitutes a threshold value with regard to a mechanical stability, in particular shore hardness. The packaging determined according to the present invention can then ensure that the product remains below this threshold value throughout the storage time (optionally including the in-use time).

The suitability indicator, which corresponds to the suitability of the packaging system for packaging the substance, is preferably calculated with at least one parameter of the packaging system relating to the environmental condition and with the stability indicator of the substance. In particular, a humidity-related parameter of the packaging system, particularly sorption data and/or permeation data, is used to calculate, estimate, predict or simulate the stability of the substance packaged by means of the packaging or packaging system associated with the parameter, by means of the stability indicator, which preferably characterizes the effect of moisture on the substance.

Preferably, stability-influencing properties of the substance, particularly a water content and/or sorption characteristics and/or sorption capacity and/or sorption kinetics of the substance, or a relevant parameter, are taken into consideration in calculating the suitability indicator and/or form or forms a part of the stability indicator. Thus, in particular, the suitability indicator, which corresponds to the suitability of the packaging system for packaging the substance, is calculated with an indicator representing the stability-influencing properties of the substance and preferably with at least one parameter of the packaging system relating to the environmental conditions and/or with the stability indicator of the substance.

Preferably, the stability indicator is determined independently of the packaging and/or the parameter or parameters of the packaging system are determined independently of the substance. In particular, the stability indicator corresponding to the stability of the substance is determined independently of a package or a packaging system. This stability can subsequently be used to determine, preferably to calculate, suitability indicators or suitabilities of packaging systems for packaging the substance. It is advantageously possible, by independent determination, to calculate the suitability indicator without having to determine specific stability indicators for different packaging systems.

The calculation of the suitability or the suitability indicator preferably involves on the one hand the stability indicator, which corresponds to the stability of the substance or of a component of the substance and on the other hand at least one parameter of the packaging system. Thus the stability indicator and the parameter of the packaging system together preferably form the basis for the calculation of the suitability indicator or the suitability of the packaging system for packaging the substance. Advantageously, the stability of the substance when packaged using the packaging system can advantageously be calculated or predicted in this way. This advantageously makes it possible to select or choose potentially suitable packaging systems and/or to discard fundamentally unsuitable packaging systems without the need for measurements or experiments in which the substance is tested after being packaged using the respective packaging system.

Preferably the stability indicator is determined, preferably measured, based on the properties of the substance. This is preferably done after the substance has been exposed to certain, preferably constant, environmental conditions over a specific length of time in an open or unpackaged state, hereinafter also referred to as an open storage study.

The stability indicator is thus preferably determined independently of a packaging system and particularly with the substance openly accessible or stored open. The advantage of this is that ambient conditions such as the ambient temperature, (relative) humidity of the environment or the like can be properly controlled or acts directly on the substance. In this way, a model representing the stability of the substance can advantageously be produced by means of which stability properties of the substance can be replicated.

The stability is or preferably forms a model for the stability of the substance, preferably taking account of one or more environmental conditions, particularly preferably as a function of the air humidity and/or temperature and/or climate and/or optionally the UV radiation and preferably the time, period or duration of storage under the ambient conditions.

Preferably, the stability indicator comprises a plurality of stability indicator values, which preferably correspond to properties of the substance after the substance has been exposed to different ambient conditions, which are preferably constant for the particular stability indicator value, and/or has been exposed over different specific time periods. The stability indicator may thus have a plurality of stability indicator values. In particular, the stability indicator is or comprises a matrix, a vector, a table, an allocation, a function, range of functions, plane and/or hypersurface or some other arrangement of a plurality of stability indicator values.

Preferably, the stability indicator or the hypersurface assigns at least one ambient condition to a (storage) time and to a degradation, degradation characteristic, or degradation level.

The particular stability indicator value is preferably determined, particularly measured, with the substance, which has been stored at constant ambient conditions, particularly at a constant temperature and/or (relative) humidity and/or climate.

Preferably, different stability indicator values correspond to different time periods over which the substance has been exposed to the environmental conditions, and/or correspond to different environmental conditions.

In particular, different stability indicator values are thus determined under constant environmental conditions for different periods of activity of the environment on the substance. This is preferably done experimentally and/or by measurement.

Preferably, a plurality of stability indicator values are determined, especially measured, (exclusively) at different ambient temperatures. In this way the stability indicator may represent (exclusively) temperature-dependent stability characteristics of the substance.

Preferably, a plurality of stability indicator values are determined, particularly measured, (exclusively) at different (relative) humidities. In this way, a stability can advantageously be represented by the stability indicator as being (exclusively) dependent on the (relative) humidity of the environment/(directly) surrounding area of the substance.

Particularly preferably, the stability indicator comprises stability indicator values for different temperatures and for different relative humidities. Alternatively or additionally, the stability indicator comprises stability indicator values for indicating a stability depending on oxygen and/or solvent concentration or stability/degradation depending thereon.

Most particularly preferably, the stability indicator has stability indicator values for different temperatures at different periods of time over which the substance has been exposed, in open or unpackaged form, to the ambient conditions at the respective temperature. Alternatively or additionally, the stability indicator comprises stability indicator values for different relative humidities of the environment/(directly) surrounding area of the substance for different defined periods of time over which the substance has been exposed, in open or unpackaged form, to the ambient conditions with the different relative humidities.

It is also particularly preferred if only one ambient condition, particularly only the temperature or only the relative humidity of the environment/(directly) surrounding area is varied. In this way, the dependencies of different ambient conditions can advantageously be determined independently of one another and used to calculate the suitability indicator.

In a preferred aspect of the present invention, a group of stability indicator values is determined, wherein, in order to determine the group of stability indicator values, only the relative humidity of the environment/(directly) surrounding area of the substance is varied and stability indicator values are determined for different periods of time over which the substance has been exposed to the particular, preferably unchanging, ambient condition. In this way, groups of stability indicator value can be determined, particularly measured, by means of which the stability of the substance depending on the ambient conditions and the length of time can be modeled in a reproducible and systematic manner.

In a preferred aspect of the present invention which may also be implemented independently, a plurality or a group of stability indicator values are determined, the group of stability indicator values being determined by varying the temperature while keeping the moisture level of the substance constant as the temperature is varied. For this purpose, preferably the relative humidity of the environment/(directly) surrounding area is adapted such that the absolute quantity of water or the number of water molecules in the substance is kept constant. It has advantageously been found that under these conditions the change in stability of the substance is caused exclusively by the temperature, as the influence of the moisture depends on the number of reactants in the form of water molecules. By adapting the relative humidity, preferably increasing or adapting the relative humidity while raising the temperature, it is ensured that the changes in the stability of the substance are dependent only on the change in temperature. It is also preferable if stability indicator values are determined for different periods of time over which the substance has been exposed to the particular, preferably unchanging, ambient condition. In this way, groups of stability indicator values can be determined, particularly measured, by means of which the stability of the substance as a function of the ambient conditions and the period of time can be modeled in a reproducible and systematic manner. Alternatively, however, the relative humidity or the absolute humidity may also be kept constant.

In an aspect which can also be implemented independently, the present invention relates to the determination of a stability indicator or a model for the stability of the substance, wherein the stability of the substance is determined as a function of different ambient conditions, preferably the relative humidity (at a particular, preferred constant or unvarying temperature, the term relative humidity according to the present invention preferably being replaceable with saturation vapour pressure or vice versa) and/or the temperature of the immediate environment/(directly) surrounding area of the substance, in particular by varying in each case only the relative humidity and the temperature with the relative humidity adjusted, so that the quantity of water in the substance remains constant, or by varying the length of time over which the substance is exposed in open or unpackaged form to the ambient conditions. The other details, which are described hereinbefore and hereinafter in connection with stability indicators, constitute preferred embodiments of this aspect, which can also be implemented independently.

The suitability indicator, which preferably corresponds to the suitability of a packaging system for packaging the substance, preferably represents or predicts the stability of the substance when packaged using the packaging system. The suitability indicator is thus preferably suited, configured or designed, to make it possible to evaluate the suitability of the packaging system for the substance. The suitability indicator may take account of, or make it possible to take account of, ambient conditions, which can be expected on the side of the packaging remote from the substance. Advantageously, in this way, it is possible to evaluate the suitability of a packaging system for a substance, or vice versa, as a function of the global markets for the packaged substance. Consequently, it is possible to select potentially suitable packaging systems for the substance or vice versa, above all without the need to carry out experiments.

The suitability indicator may comprise a plurality of suitability indicator values which correspond to properties of the substance or predict properties of the substance after the substance has been stored as packaged using the packaging system, particularly over different defined periods of time and/or under defined external influences.

Consequently, the suitability indicator preferably replicates the stability characteristics of the substance in its packaged state. Accordingly, different packaging systems can be compared and evaluated, using or by means of the suitability indicator, as to whether the stability requirements are met or can be met.

The suitability indicator is preferably calculated by extrapolating, interpolating and/or predicting the behavior when the substance is packaged using the packaging system, with the stability indicator and with the parameter or parameters of the packaging system. Thus the calculation preferably mathematically links the preferably packaging-independent stability indicator with the preferably substance-independent parameter(s) of the packaging system so as to calculate the stability of the substance during storage after packaging with the packaging system.

Preferably, the suitability indicator is calculated by simulating the stability of the substance in the packaged state. It is preferable if the stability indicator of the substance and the parameter of the packaging system form input variables for a simulation of this kind. A simulator may be provided which determines or calculates an environment obtained within the packaging, with corresponding environmental characteristics, using the properties of the packaging system, which may be represented by the parameter of the packaging system. Moreover, the interactions between the substance arranged in the package and the environment for the substance resulting from the substance and the properties of the packaging are preferably determined, particularly taking account of any interactions or the effect of the substance on its environment and taking account of the influence of the packaging on the environment/(directly) surrounding area of the substance.

Thus, colloquially speaking, a microclimate in the packaging is calculated taking into account the relevant influencing factors, and conclusions are drawn using the stability indicator as to the effects on the stability of the substance.

The suitability indicator and/or the stability indicator preferably correspond at least to a degradation characteristic or degradation tendency of the substance, preferably to a degradation characteristic or degradation tendency dependent on the ambient conditions. This may relate to a physical degradation of the substance, for example, a reduction in the breaking strength or the like. Alternatively or additionally, it may be a chemical degradation characteristic or tendency, for example a loss of active substance.

The suitability indicator and/or stability indicator may correspond to a chemical stability of the substance or of a component of the substance, particularly a dissolution or decomposition, and/or the mechanical stability (of the formulation) of the substance, particularly a breaking force or a tendency to disintegration or a degree of disintegration and/or to the stability of distribution of different ingredients in the substance. Preferably, the suitability indicator and/or the stability indicator corresponds both to a physical and to a chemical stability of the substance when the substance is packaged using the packaging system. In this way the suitability of a packaging system for the substance can be evaluated much more precisely.

In an aspect of the present invention, which may also be implemented independently, the suitability indicator and/or the stability indicator simultaneously correspond to a chemical and a mechanical stability of the substance. It is clear, from the example of the substance in the form of a medicament in tablet form, that the suitability of a packaging system both depends on the fact that the tablet remains mechanically intact when taken, i.e. is not fragmented, and on the other hand also remains chemically intact, i.e. the concentration of active substance is still sufficient and no harmful substances have formed. The suitability indicator and/or the stability indicator preferably takes account of both chemical and mechanical stability properties of the substance. Consequently, the suitability indicator and/or the stability indicator makes it possible to carry out comprehensive evaluation or selection of suitable packaging systems for a substance, while avoiding the possibility, during subsequent experimental verification, that the packaging system is unsuitable for packaging the substance because of criteria for the stability of the substance which have not been taken into account and consequently leading to unnecessary additional experimental investigations.

A (variable) ambient condition is or is determined preferably by a humidity, particularly a (relative) humidity and/or a temperature, particularly an ambient temperature, or has one such. However, it is also possible for other or additional (variable) ambient conditions to be used or taken into consideration. For example, the irradiation of light, UV other radiation may be or constitute an ambient condition. However, other ambient conditions are also alternatively or additionally possible. Preferably, however, at least the relative humidity and the temperature are taken into account or are variable for determining the stability indicator and/or as a basis for the parameter of the packaging system and/or to calculate the suitability indicator. Under constant ambient conditions, preferably, ambient conditions, which have not been explicitly stated, or other such conditions are kept constant or are invariable.

The packaging system is preferably characterized by means of at least one and preferably several parameters. Preferably, the permeation rate or the sorption rate and/or the sorption capacity and/or sorption kinetics of a packaging material, and particularly each form a parameter of the packaging system.

The permeation here preferably represents the possibility of the ingress and egress of moisture or substances through the packaging material, particularly as a result of or in the event of concentration gradients. Preferably, the permeation is based on the diffusion, particularly of water vapor. The permeation or diffusion depends particularly on the difference in concentration in water or water vapor between an inner space and the surroundings of a package.

The sorption or sorption capacity of the packaging system represents the storability of the packaging material for moisture or substances and may represent an ingress of moisture during packaging or during the packaging process. It may be taken into account that the packaging material as such may contain moisture or moisture can enter the packaging during the packaging process. Alternatively or additionally, desorption properties may also be taken into account or form a parameter of the packaging system.

The packaging system is thus preferably characterized or modeled by means of at least one but preferably a number of parameters and/or by means of parameters relating to the introduction of moisture during storage/permeation and/or the introduction of moisture during packaging/absorption. The parameters of the packaging system may represent or form a model of the packaging system, at least in respect of the moisture ingress and/or egress.

It is particularly preferable for the stability indicator to have a plurality of stability indicator values relating to different ambient conditions and for the calculation of the suitability indicator to be calculated with these stability indicator values and with a plurality of parameters of the packaging system relating to the specific ambient conditions, while the parameters of the packaging system may represent characteristics of the packaging system with regard to different ambient conditions.

In another aspect of the present invention which may also be implemented independently, one or more packaging systems for a substance is or are selected, while a suitability indicator for the at least two different packaging systems is calculated by the proposed method. The suitability indicators calculated are preferably compared with one another and/or with at least one target value. Preferably, using the results of the comparison, one or more of the packaging systems is or are selected and/or discarded automatically, indicated by an indicator or displayed, particularly printed out, or sent in the form of an electronic message or stored. In this way a time-saving fully automatic pre-selection of potentially suitable packaging systems for a particular substance can be obtained.

Another aspect of the present invention which can also be implemented independently relates to a system for calculating a suitability indicator which corresponds to the suitability of a packaging system for packaging a substance, the system being configured to carry out the proposed method. Corresponding advantages can be achieved in this way.

Preferably, the system comprises an input device for inputting a stability indicator of a substance as a function of at least one ambient condition. In particular, the inputting device may be a measuring device.

The measuring device may be configured to measure the stability indicator or one or more stability indicator values. For this purpose the measuring device may be configured to carry out chemical and/or physical analysis.

In particular, the measuring device is and/or comprises: a device for determining the mechanical stability, breaking force or the like, a mass spectrometer or other analyzer for determining the chemical composition or a fraction or an absolute quantity of a component of the substance, particularly the active substance in the case of a drug, a moisture meter for determining the water content of the composition or the like.

Preferably, the system also comprises a calculating or computing device for calculating the suitability indicator with at least one parameter of the packaging system relating to the ambient condition and with the stability indicator of the substance.

The system preferably comprises a packaging system database in which at least one parameter specific to a packaging system, and preferably a plurality of parameters which are specific to a plurality of packaging systems are stored or deposited.

The calculating device is preferably configured to read out the parameter or parameters from the packaging system database in order to calculate the suitability indicator and to link it to the stability indicator mathematically, particularly in such a way that the stability of the substance packaged using the packaging system and/or the suitability of the packaging system for packaging the substance is or can be calculated.

It is preferred that the suitability indicator is calculated independently of the packaging system and/or by storing the substance in the unpackaged state. Alternatively or additionally, the parameter relating to the ambient condition corresponds to a sorption characteristic/comprises sorption data and/or corresponds to a permeation property/comprises permeation data of the package or packaging material of the packaging system.

Preferably the ambient condition of the substance being packaged in the packaging system is calculated. The ambient condition of the substance packaged in the packaging system preferably is calculated with the at least one parameter of the packaging system relating to the ambient condition, and the suitability indicator is calculated with the ambient condition that has been calculated. Thus, ambient conditions resulting inside the package are determined and used to determine the stability of the substance, represented by the stability indicator.

A further aspect of the present invention, which can be realized independently as well, relates to calculating a suitability indicator, which corresponds to a suitability of a packaging system for packaging a substance, preferably a development over time of the uptake of water by the substance packed by means of the packaging system and/or a development over time of a degradation of the substance packed by means of the packaging system, wherein the suitability indicator is calculated on the basis of a stability indicator which corresponds to a physical and/or chemical stability of the substance or of a component of the substance, on the basis of sorption characteristics of the substance and on the basis of sorption data and permeation data of a package or packaging material of the packaging system.

It is particularly preferred that the parameters of the packaging system or the packaging material of the packaging system, preferably together with sorption characteristics or sorption data of the substance or parameters corresponding thereto, form a model, overall model, preferably a permeation model or a part thereof, in the following alternatively referred to as SynPD model or SynPD concept. SynPD means Synergy in Package and Product Development, which preferably is or comprises a particular method, (simulation) model, and/or system.

Using the model, ambient conditions of the substance packaged in the packaging system are calculated. In particular, using the ambient conditions calculated for the substance packaged in the packaging system, an influence on the substance, preferably a development over time, particularly of an uptake of water or of a water content of the substance, is or are calculated. The suitability indicator is calculated using the model and/or the calculated influence of the calculated ambient conditions on the substance, preferably based on the stability indicator.

According to a further aspect of the present invention, sorption characteristics and/or the stability indicator of the substance are determined independently of the sorption data and permeation data of the package V or packaging material of the packaging system. Alternatively or additionally, that sorption data and permeation data of the package or packaging material of the packaging system are determined independently of the sorption characteristics and/or the stability indicator of the substance.

A further aspect of the present invention, which can be realized independently as well, relates to a method for selecting and/or automatically determining one or more packaging systems for a substance, particularly a medicament, wherein a packaging system is determined or selected and/or the suitability indicator is calculated using a model having at least permeation data and sorption data of a package or one or more packaging materials of the packaging system and sorption characteristics of the substance or corresponding parameters.

Preferably, a combination of packaging material or packaging materials and the geometric shape of the packaging material(s) forming the package is selected or determined, preferably so that the combination is suitable for packaging the substance and enables subsequent storage to take place under certain climatic conditions over a given period of time without any degradation of the substance exceeding a certain threshold when stored under these conditions in the packaged state.

In particular, the packaging system and/or the package is or are characterized at least by the chemical composition of one or more packaging materials and by a geometric shape of the packaging material or materials and, preferably, also by process conditions of the packaging process or its effects on the substance and/or the packaging materials and/or by the atmosphere enclosed together with the substance during the packaging process.

The package and/or the packaging material can be characterized by its chemical composition and a geometric shape, while preferably sorption data and permeation data of the package or packaging material take account of both the chemical composition and the geometric shape.

Preferably, sorption data and/or sorption characteristics comprise, or are represented by, sorption isotherms or sorption capacities. Further, preferably, permeation data comprise, or are represented by, a permeability or permeation rate, particularly in respect of water.

A further aspect of the present invention, which can be realized independently as well, relates to a system for calculating a suitability indicator which corresponds to a suitability of a packaging system for packaging a substance, and/or for selecting and/or automatically determining one or more packaging systems, the system being configured to carry out a method according to the present invention.

A further aspect of the present invention, which can be realized independently as well, relates to a method for determining a stability indicator which corresponds to a physical and/or chemical stability of a substance or of a component of the substance, wherein the physical and/or chemical stability depends on multiple stability influencing factors/ambient conditions, wherein the stability indicator is determined depending on one particular of the stability influencing factors and/or ambient conditions while further or the remaining stability influencing factors and/or ambient conditions are kept unvaried.

In particular wherein the stability influencing factors or ambient conditions comprise or consist of comprise a relative humidity of the ambient or atmosphere being in direct contact with the substance, and/or an absolute water content of the substance, and/or the temperature of the substance.

Preferably, the stability indicator is a function and is determined depending on time, preferably, thus the stability indicator indicating a physical and/or chemical stability of the substance or of a component of the substance as a function of both time and the particular one of the stability influencing factors, in particular wherein the function is expressed, expressable, interpolated and/or interpolable as a hypersurface, and/or is unique, in particular one-to-one.

The stability indicator for a particular point in time preferably is calculated by means of determining a progress or function of the particular stability influencing factor over time and projecting the progress or function of the stability influencing factor to or substituting it in the stability indicator.

An influence on the substance of the ambient conditions—relative humidity of atmosphere being in direct contact with the substance and temperature—are determined independently of one another, preferably by storing the substance at varying relative humidity while keeping the temperature unvarying and/or by storing the substance varying the temperature while keeping the absolute water content of the substance unvarying or compensating for any influence of water variation on the stability of the substance.

A further aspect of the present invention, which can be realized independently as well, relates to determining a packaging system, the packaging system comprising a package or at least one or more packaging materials for packaging a substance, wherein a permeation behavior of the packaging material in a particular shape for packaging the substance (3), in particular a deep drawn shape, is determined and/or considered.

A further aspect of the present invention, which can be realized independently as well, relates to determining a packaging system, the packaging system comprising a package or at least one or more packaging materials for packaging a substance, wherein sorption data and/or a water content of the packaging material is or are considered, preferably in addition to sorption characteristics and water content of the substance.

A further aspect of the present invention, which can be realized independently as well, relates to determining a packaging system, the packaging system comprising a package or at least one or more packaging materials for packaging a substance, wherein a suitability indicator is determined and/or considered.

A further aspect of the present invention, which can be realized independently as well, relates to determining a packaging system, the packaging system comprising a package or at least one or more packaging materials for packaging a substance, wherein a stability indicator (3) according to the present invention is determined and/or considered.

A further aspect of the present invention, which can be realized independently as well, relates to determining a packaging system, the packaging system comprising a package or at least one or more packaging materials for packaging a substance, wherein a chemical structure of the packaging material, and/or geometrical properties of the packaging material, and/or preconditioning requirements for the packaging material, and/or preconditioning requirements for the substance, and/or an amount of drying agents to be placed inside the package (V) together with the substance (3), and/or an amount of auxiliary materials being part of substance (3) or which is to be placed inside the package (V) together with the substance (3) is or are considered and/or determined, preferably calculated based on a model (15) and/or with a simulation environment, automatically, and/or iteratively.

A further aspect of the present invention, which can be realized independently as well, relates a simulation environment for determining a packaging system for packaging a substance and/or for determining a suitability of the packaging system to achieve a preset stability of the substance when packaged with the packaging system, in particular represented by a stability indicator, characterized in that the simulation environment is configured to carry out the steps of one or more methods according to the present invention.

A further aspect of the present invention, which can be realized independently as well, relates to determining a stability indicator which corresponds to a physical and/or chemical stability of the substance or of a component of the substance, wherein a set of multiple samples of the substance are examined at the same time under different ambient conditions.

Particularly preferably, a particular one or more of the samples of the substance is or are exposed to conditions where a minimum stability of the samples of the sample set can be expected.

In particular, a maximum temperature within the sample set, and/or a maximum relative humidity within the sample set, and/or a maximum light or UV radiation within the sample set, and/or further maximum or worst case stability influencing factors within the sample set is or are applied to the particular one or more of the samples of the substance.

According to a preferred aspect of the present invention, one or more of the particular one or more samples is examined at several subsequent time-points until a stability degradation of the particular one or more samples or a degradation exceeding a limit is determined.

Preferably, only after this determination of degradation of the particular one or more samples or a degradation exceeding a limit, one or more of the further samples of the set are examined as well.

This provides the advantage of reducing the effort for examining samples and the number of samples needed to be stored under particular conditions can be reduced. Thus, less climate chambers, storage areas and energy are required. Thus, the stability indicator can be determined more efficiently.

A further aspect of the present invention, which can be realized independently as well, relates to a computer-readable storage medium or computer program product comprising program code means which when executed are configured to carry out the steps of the method of the present invention.

The various aspects of the present invention may be implemented and advantageous both individually and in any desired combination with one another.

Figure 2:
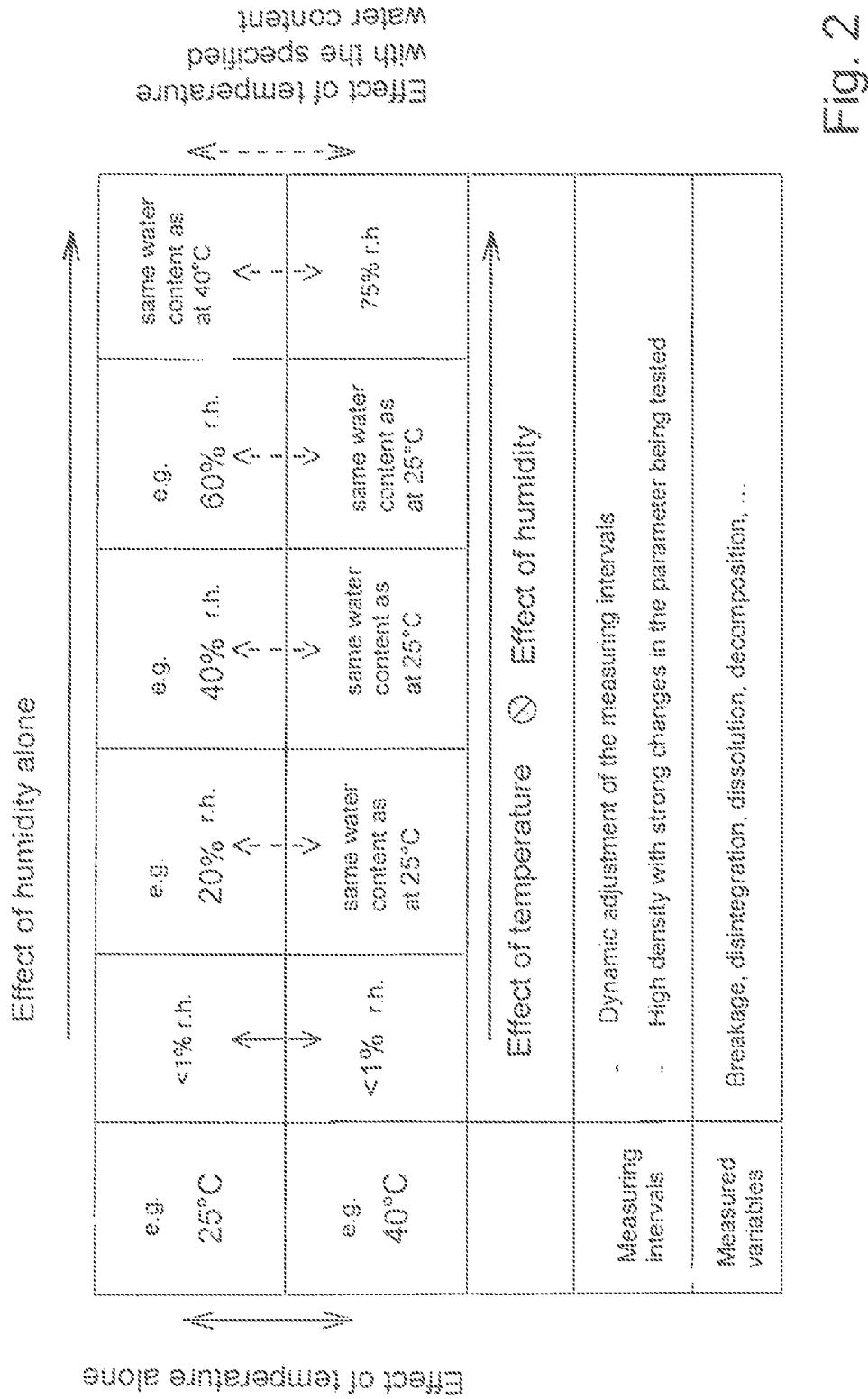
Figure 3:
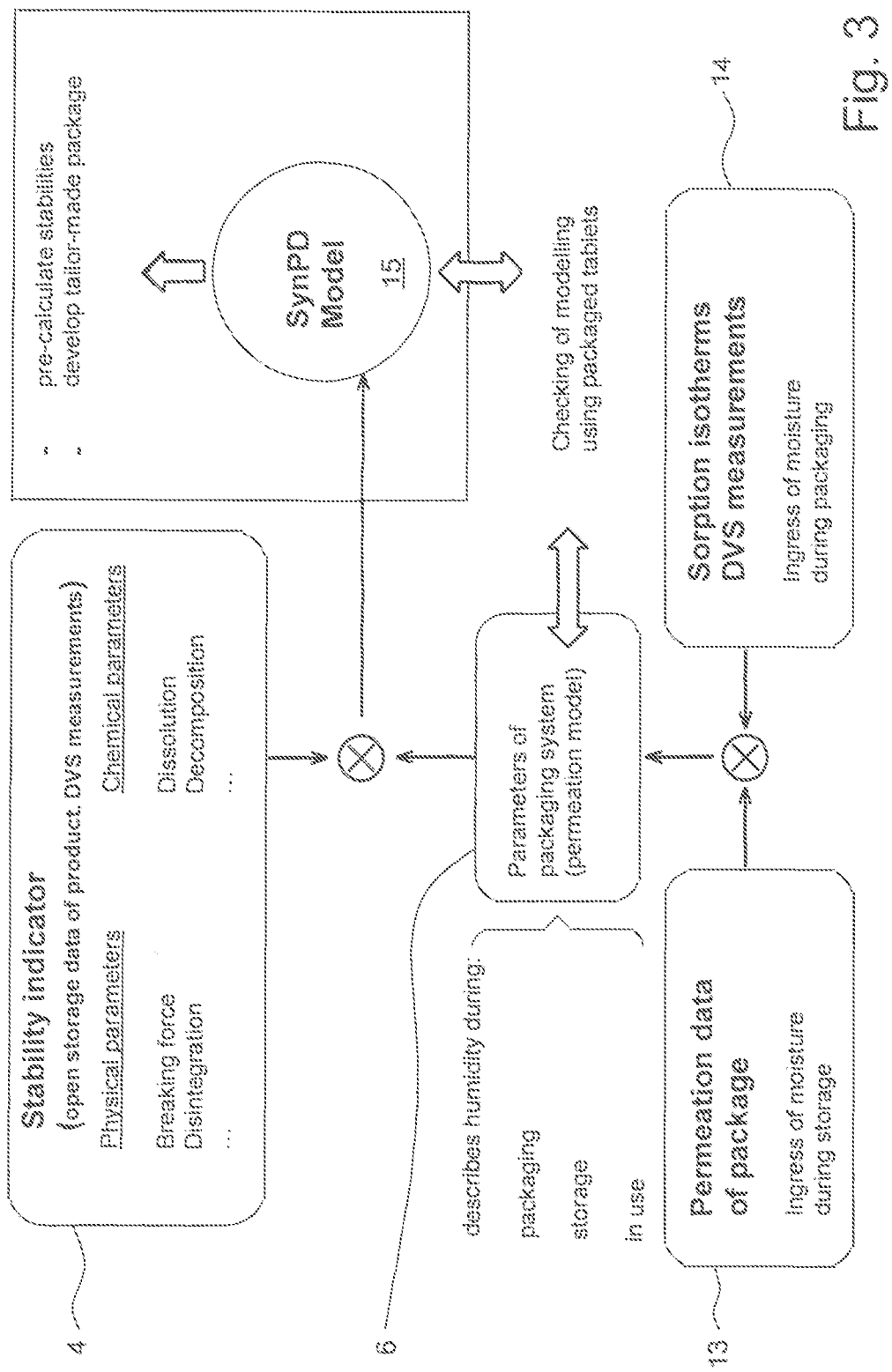
Figure 4:
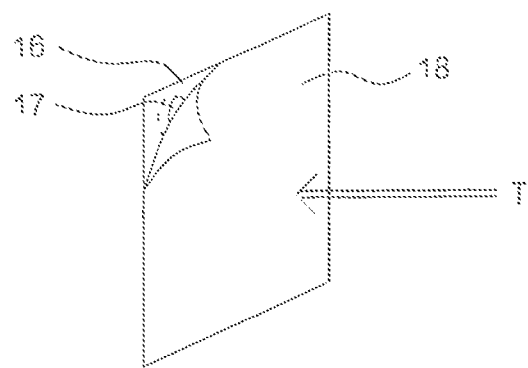
Figure 5:
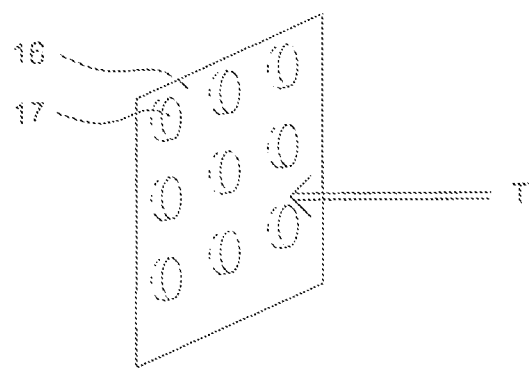
Figure 6:
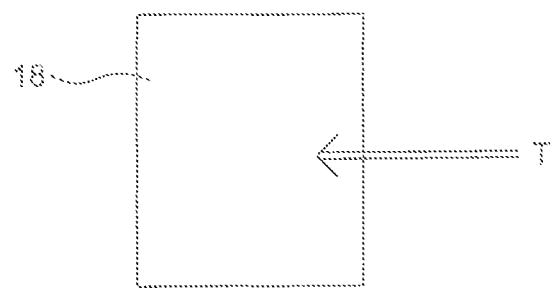

Further aspects, advantages and properties of the present invention will become apparent from the claims and the following description of an embodiment exemplifying the present invention by reference to the drawings, wherein:

FIG. 1 a system for calculating a suitability indicator;
FIG. 2 a diagram by way of example for determining the stability indicator in the proposed manner;
FIG. 3 a diagram of the proposed method;
FIG. 4 a package;

FIG. 5 a part of the package from FIG. 4;

FIG. 6 another part of the package from FIG. 4; and

Figure 7:
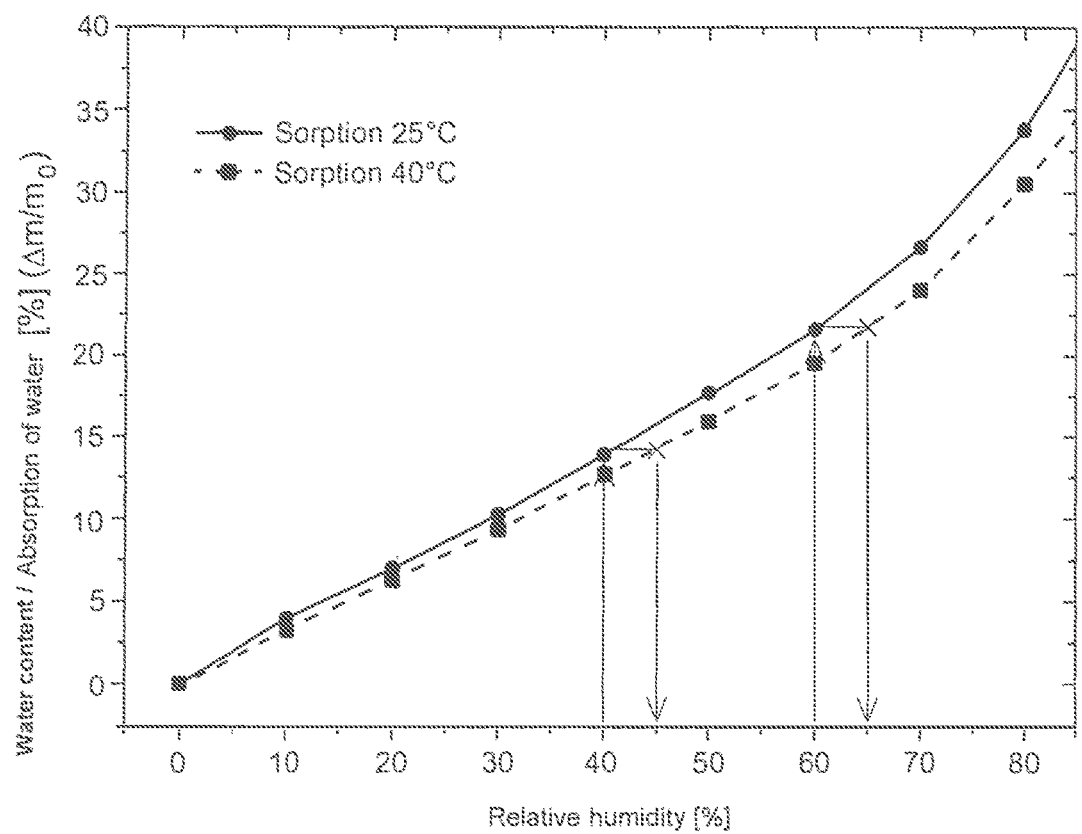

FIG. 7 a sorption diagram.

In the description that follows, the same reference numerals are used for identical or similar parts where identical or similar advantages or properties can be achieved, even though the description has not been repeated.

FIG. 1 shows a system S for calculating a suitability indicator 1 which corresponds to the suitability of a packaging system 2 for packaging a substance 3.

A stability indicator 4 preferably corresponds to a stability of the substance 3 or a component thereof. The stability indicator 4 is preferably determined as a function of at least one ambient condition 5, preferably a specific relative humidity and/or a specific temperature of the environment of the substance 3, preferably while maintaining a constant absolute moisture level of the substance 3.

The ambient condition 5 alternatively or additionally is an oxygen concentration and/or a solvent concentration, an (UV) radiation level or the like.

According to one aspect of the present invention the suitability indicator 1 can be calculated using the stability indicator 4 and at least one parameter 6 of the packaging system 2. For this purpose it is preferable if the stability indicator 4 is linked to the parameter 6 of the packaging system 2 by means of a mathematical link 7. This is preferably done by means of a calculating device, a computer, a microcontroller or the like.

Preferably, the link 7 is made such that, starting from the ambient condition 5 on which the stability indicator 4 is based, conclusions can be drawn as to corresponding ambient conditions which arise when the substance 3 is packed using the packaging system 2 inside the package V in the region of the substance 3.

Using the link 7, the suitability indicator 1 is preferably calculated which corresponds to a suitability of the particular packaging system 2 for packing the substance 3.

The substance 3 is preferably a medicament, particularly with at least one active substance and/or at least one excipient. The substance 3 is preferably present as a solid. Alternatively or additionally, however, the substance 3 may also be or comprise a liquid, suspension or the like.

The substance 3 is preferably present in the form of a plurality of discrete units. The substance 3 is preferably characterized in the form of these several discrete units or in the form in which the substance is to be packed.

Preferably, for determining the stability indicator 4, the substance 3 is characterized in a, particularly physical, form or presentation, particularly tablet form, which is identical to the form in which the substance 3 can be packed using the packaging system 2.

In the embodiment shown, the substance 3 is present in the form of dry compacted material, in the form of tablets or in the form of capsules. However, other solutions are also possible.

According to an aspect of the present invention which can also be implemented independently, it is envisaged that, for determining the stability indicator 4, the substance 3 is exposed, in the open or unpackaged state, to a specific ambient condition 5 over a given or specified length of time. For this purpose the system S may comprise a climate-controlled apparatus 8 or the like.

The climate controlled apparatus 8 may be configured to adjust and/or keep constant at least the temperature and/or relative humidity in a chamber of the climate controlled device 8. The substance 3 is preferably arranged in the climate controlled device 8 or in the chamber thereof and is exposed in the open state, over a certain length of time, to at least substantially constant ambient conditions 5, particularly preferably a constant temperature and/or a constant relative humidity. This has the advantage that the stability indicator 4 thus determined can operate as a model or that, on the basis of the stability indicator 4, stability properties can be determined or extrapolated as a function of specific constraints or ambient conditions.

Alternatively or additionally, however, it is also possible for the substance 3 to be exposed to certain developments of the ambient condition 5. In particular, it is possible for the substance 3 to be exposed in the open state to a certain development of one or more of the ambient conditions 5. For example, the temperature and/or the relative humidity of the ambient condition 5 may be varied in a gradient, alternately or the like and/or over a certain period of time. However, this is preferably done in addition to investigations on the substance 3 which is exposed in the open state over a defined period of time to at least substantially constant ambient conditions 5, particularly preferably a constant temperature and/or a constant relative humidity.

After the substance 3 has been exposed to the ambient condition 5 over the defined length of time, the properties or changes in the properties of the substance 3 are preferably characterized or determined, particularly measured.

The system S may comprise a measuring device 9 for determining chemical and/or physical properties of the substance 3. In particular, the system S may comprise a measuring device 9 for measuring the mechanical stability or breaking force. Alternatively or additionally, the system S may comprise a measuring device 9 for determining chemical parameters 6, particularly a measuring device 9 for determining absolute or relative quantities of ingredients of the substance 3. Particularly preferably, the system S is configured to determine an amount of active substance in a medicament.

The measuring device 9 is preferably configured to display the physical and/or chemical properties of the substance 3 as a stability indicator 4. The stability indicator 4 may be stored, intermediately stored or filed in an optional database 10 or by some other method. Alternatively or additionally, the stability indicator 4 is further processed directly or combined or linked, particularly mathematically, with parameters of the packaging system 2 to form a common model.

Particularly preferably, the stability indicator 4 represents a behavior of the substance 3 as a function of the ambient condition 5 and/or the time. The stability indicator 4 is preferably a model, particularly at least with regard to the changes in the substance 3 in respect of its physical and/or chemical properties as a function of a storage period under specific ambient conditions 5.

The determining of the stability indicator 4 or the modeling of the physical and/or chemical behavior of the substance 3 in the unpackaged state of the substance 3 or independently of a packaging system 2 constitutes an aspect of the present invention which can also be implemented independently.

Preferably, the stability indicator 4 comprises a plurality of stability indicator values 11. The stability indicator values 11 preferably correspond to physical and/or chemical properties of the substance 3, after the substance 3 has been exposed in the open state to the ambient conditions 5 over a defined period of time.

According to one aspect of the present invention it is preferable if the ambient conditions 5 are kept constant for the stability indicator value 11 in question or if the ambient conditions 5 are invariable in order to determine a stability indicator value 11.

It is also preferable if a plurality of stability indicator values 11 are determined while, for a second of the stability indicator values 11, compared to a first of the stability indicator values 11, only one ambient condition 5 is changed, particularly the relative humidity of the environment of the substance 3, and the substance 3 is exposed unaltered to the changed ambient conditions 5 over a certain length of time. It is also preferable if the ambient conditions 5 are kept constant or unchanged over the period of time. Then corresponding stability indicator values 11 can be determined or measured.

In an aspect which can also be implemented independently it is preferable if a plurality of stability indicator values 11 are determined, while for a second one of the stability indicator values 11, by comparison with a first of the stability indicator values 11, the temperature is changed while the water content in the substance is kept constant. For this purpose the relative humidity of the environment of the substance 3 is adapted so that in spite of the change in temperature an equilibrium is established between water molecules entering and exiting the substance 3 preferably such that the absolute water content of the substance 3 remains unchanged. The substance 3 is preferably exposed to the altered ambient conditions 5 over a certain length of time without changing. It is also preferable if the ambient conditions 5 are kept constant or are unchanged over the length of time. Then corresponding stability indicator values 11 can be determined or measured.

In the aspect which can be implemented independently, relating to the determination of the stability indicator 4 or the modeling of the substance behavior, it is thus particularly preferable to determine, particularly to measure the substance 3, in an open storage study, stability properties or stability indicator values 11 which are different over one or more different periods of time but remain constant for the respective measurement.

FIG. 2 shows in connection with this a preferred diagram by means of which stability indicator values 11, in particular, can be determined.

The first two lines relate to tests or series of tests in which the substance 3 is exposed to certain ambient conditions 5. Between the individual experiments, each represented by a field, preferably only one ambient condition or only the temperature is changed while the water content of the substance 3 remains constant. The first line relates to the changes in the relative humidity at a constant temperature of 25° C. However, other temperatures may also be chosen, particularly as a function of the later ranges of use of the substance 3 packaged by means of the packaging system 2 or other preconditions.

A first experiment (second field in the first line) can be carried out at a first temperature and at a first relative humidity, in this case at 25° C. and at less than 1% relative humidity. For a second experiment the relative humidity may be selected to be different from that in the first experiment and, in this example, at 20% relative humidity. Other experiments may be carried out at a constant temperature and other relative humidities, in the example shown at 40% relative humidity and 60% relative humidity. In this way it is possible to obtain a series of measurements or a group of stability indicator values 11, with only the relative humidity being varied in terms of the ambient conditions 5. In this way the effect of humidity alone can be determined or characterized, i.e. the effect of changing the relative humidity while keeping the temperature constant.

It is also preferable if experiments are carried out at a second temperature which is different from the first temperature. In the embodiment shown the second line relates to measurements or a series of measurements at an altered temperature of 40° C., in particular. However, a different temperature may also be used.

One particular feature of the present invention is that, for measurements at an altered temperature, the water content of the substance is kept constant. It is thus preferable to carry out further measurements or to determine further stability indicator values 11 at a second temperature different from a first temperature, while the water content of the substance 3 is kept constant in comparison to a corresponding measurement at a first or other temperature, in this case 25° C. This makes it possible to draw conclusions as to the effects of temperature alone. By means of corresponding measurements with the same absolute quantity of water in the substance 3 and different temperatures, the effect on the stability of the substance 3 can be determined, which depends exclusively on the change in temperature. Alternatively or additionally, however, it is also possible to carry out series of measurements in which the relative or absolute humidity is kept constant while tests are carried out at different temperatures.

Overall, it is preferable if the stability indicator 4 has a plurality of stability indicator values 11, each corresponding to the same temperature. Alternatively or additionally, it is preferable if the stability indicator 4 has a plurality of stability indicator values 11 which correspond to the same absolute quantity of water in the substance 3. Most particularly preferably, the stability indicator 4 comprises at least a few stability indicator values 11 corresponding to the same temperature and/or at least a few stability indicator values 11 corresponding to the same absolute quantity of water in the substance 3. In this way the stability characteristics of the substance 3 depending on the temperature and/or humidity can advantageously be modeled independently of one another.

The respective stability indicator values 11, experiments or measurements may correspond to one or more different periods of time over which the substance 3 is exposed to the respective ambient conditions 5. It is preferable if the stability indicator values 11 at the different temperatures and/or humidities at a constant temperature correspond to the same period of time. If a number of different periods of time are provided it is particularly preferable if the respective stability indicator values 11 at the different temperatures and/or humidities and at constant temperature comprise information corresponding to identical periods of time.

In the specific embodiment it may thus be envisaged that, with reference to this, the substance 3 is stored open at a temperature of 25° C. and a relative humidity of less than 1% initially over a first period of time, for example 3 months, and secondly over a second period of time, for example 6 months, and corresponding stability indicator values 11 are determined. The same may be done at a different relative humidity, for example 20%, and/or at a different temperature, for example 40° C. Particularly preferably, at least three different periods of time or measuring intervals are used, with constant ambient conditions 5, particularly at constant temperature and absolute or relative humidity of the environment of the substance 3, and/or stability indicator values 11 are determined for them.

As already mentioned previously, the stability indicator 4 may be filed in a database. Alternatively or additionally, it may be a file, a matrix structure, a vector or the like. The stability indicator 4 may alternatively or additionally also form a distributed structure or comprise a plurality of not necessarily correlated stability indicator values 11. The stability indicator values 11 may also be generated, filed, stored or processed individually or independently of one another. Preferably, even in cases where the stability indicator values 11 are not stored in a directly correlated manner or form a unified file, the term stability indicator 4 is still used. However, a stability indicator 4 is preferred which has a structure that takes account of a shared characteristic, particularly the stability indicator values 11.

Preferably, the stability indicator 4 comprises several groups of stability indicator values 11. These groups may contain information corresponding to different time periods over which the substance has been exposed to the respective, preferably invariable, ambient conditions.

A group of stability indicator values 11 of this kind corresponds particularly to a fixed temperature and a fixed moisture content of the environment at different periods of time over which the substance is exposed to the respective, preferably invariable, ambient conditions.

The stability indicator 4 preferably comprises, alternatively or additionally, one or more groups of stability indicator values 11, the stability indicator values 11 corresponding to different temperatures, while the moisture level of the environment or the water content of the substance 3 and/or the period of time over which the substance has been exposed to the respective ambient condition, are unchanged.

Alternatively or additionally, the stability indicator 4 may comprise one or more groups of stability indicator values 11 at which exclusively the moisture, particularly the absolute moisture, of the environment is different in individual members of the group, but the temperature of the environment and/or the period of time over which the substance 3 has been exposed to the respective, preferably unchanged, ambient conditions 5 are unchanged or constant. Members of the individual groups may also be assigned to different groups.

In order to determine the stability indicator 4 or the stability indicator values 11, preferably physical and/or chemical properties or changes in the substance 3 are determined, preferably measured.

Particularly preferably, parameters are determined which characterize breaking strengths, a degree of disintegration, dissolution and/or decomposition of the substance 3. The stability indicator 4 or stability indicator values 11 preferably comprises or comprise corresponding parameters. These are preferably assigned to the respective ambient conditions 5 and/or to the periods of time over which the substance 3 was exposed to the ambient conditions 5. The stability indicator 4 may, in particular, be or comprise a table or tabulated structure in which measured values or other parameters, particularly relating to breaking strength, degree of disintegration, dissolution and/or decomposition, are assigned to the respective, preferably constant ambient conditions 5 and the period of time over which the substance 3 was exposed to these ambient conditions 5.

Compared with known processes in which the already packaged substance is examined, the proposed method has advantages, on the one hand, owing to the fact that the influence of the temperature and the humidity of the environment of the substance 3 can be included in the calculations independently of one another and thus the effect of the individual parameters crucial to stability can be considered and taken into account separately. Moreover, the proposed method prevents the influence of the ambient conditions 5 from being mixed with the influence of the packaging system 2 as such, particularly as a result of moisture or the like contained in the packaging materials.

FIG. 3 shows the determination or calculation of the suitability indicator 1 by means of a diagram in more detail.

The open storage data for the product preferably correspond to the stability indicator 4 of the substance 3 or vice versa. The permeation model preferably corresponds to the parameter or parameters 6 of the packaging system 2 or vice versa. Alternatively or additionally, the permeation model, particularly on the basis of the stability indicator 4 and the parameters 6 of the packaging system 2, represent the development of a (relative) humidity, the water content and/or other properties of the substance 3 which affect its stability, preferably when the substance 3 is packed in the packaging system 2. However, it is preferable if the sorption characteristics of the package V which are additionally present in the permeation model are taken into consideration and the parameter(s) 6 of the packaging system 2 go beyond pure permeation data and, in particular, comprise parameters relating to the sorption characteristics or sorption capacity of the package V. The stability indicator 4 preferably comprises a parameter relating to stability-influencing properties of the substance 3, particularly corresponding to a water content and/or sorption characteristics and/or a sorption capacity of the substance 3. Such a parameter, as part of the stability indicator 4 or independently thereof, preferably forms part of the permeation model or is taken into consideration in deciding on the package V.

One aspect of the present invention which can also be implemented independently relates to the generation and composition of the parameter or parameters 6 of the packaging system 2, while both permeation data of the packaging system and data relating to sorption isotherms are taken into consideration. This preferably makes it possible to create a model for the packaging system 2 or a permeation model in which the ingress of moisture through the packaging during storage and additionally the ingress of moisture during or as a result of the packaging of the substance 3 are taken into account.

By sorption characteristics in the sense of the present invention are meant, in particular, the property and propensity to absorb or release water vapor from the air, in particular until a state of equilibrium is achieved. The sorption isotherm, which can also be shown graphically, represents the correlation between the water content of a product and the relative humidity of the ambient air at a particular temperature.

In the present case, the water contents and/or sorption isotherm/characteristics of the packaging system 2 is of particular importance as the total moisture available within the package is influenced by the release of water from the packaging material and/or the absorption of water into the packaging material of the packaging system 2. Alternatively or additionally, the water content and/or the sorption isotherm/characteristics of substance 3 is relevant and considered.

The packaging system 2 is preferably designed to package the substance 3 in at least a substantially airtight manner. However, it depends on the packaging material whether moisture is able to pass through the packaging material, particularly by diffusion, during storage. This property can be represented by the permeation data 13.

According to an aspect of the present invention which can also be implemented independently, the parameter or parameters 6 of the packaging system 2 comprise both permeation data 13 and sorption data 14. It has been found that, advantageously, simultaneously taking account of permeation data 13 and absorption data 14 makes it possible to determine or model the characteristics of a packaging system 2 or the parameters 6 characterizing the packaging system 2 substantially more precisely.

The sorption data 14 used are, particularly preferably, sorption isotherms, as these already take account of the temperature dependency of the sorption characteristics. In this way, the sorption characteristics of a package in the packaging system 2, which vary at different temperatures, can be included in the calculation of the suitability indicator 1. This advantageously results in a substantially more accurate prognosis of the stability characteristics of the substance 3 when packaged using the packaging system 2.

The parameter or parameters 6 of the packaging system 2 are preferably used together with the stability indicator 4 to calculate the suitability indicator 1. For this purpose the stability indicator 4 may be mathematically linked to the parameter or parameters 6 of the packaging system 2.

The stability indicator 4 preferably comprises at least sorption characteristics, particularly the sorption capacity and/or sorption isotherms, of the substance 3. The sorption characteristics or the sorption capacity and/or sorption isotherms are preferably mathematically linked to the parameters 6 of the packaging system. In this way the permeation model can be formed and/or the package V or the suitability indicator 1 can be determined.

The stability indicator 4 is preferably used to calculate the stability of the substance 3 when packaged using the packaging system 2, on the basis of the permeation model.

Particularly preferably, the stability indicator 4 is included with the parameter 6 of the packaging system 2 in an overall model or permeation model, hereinafter consistently referred to as the SynPD model 15 or simulation model. The terms SynPD model 15 and simulation model are preferably interchangeable, while in the following description the term SynPD model is always used without restricting the general validity. The SynPD model 15 preferably comprises parameters that characterize the environment, particularly corresponding to climatic zones, operating times, temperature fluctuations or the like. The SynPD model 15 preferably comprises at least the stability indicator 4 and the parameter 6 of the packaging system 2. However, the SynPD model 15 may alternatively or additionally also contain other information or parameters. The combining of the stability indicator 4 with the parameter 6 has the advantage of providing a compact model for calculating the stability properties of the substance 3 and the properties of the packaging system, particularly in terms of the moisture ingress. This advantageously allows structured calculation and data management thereof. Alternatively or additionally, the parameter or parameters 6 of the packaging system 2 and/or the stability indicator 4 may, however, also be used independently of one another or in isolation.

SynPD model 15 or simulation model is preferably configured to model one or more packaging processes. If the moisture balance and/or the decomposition kinetics are known, the packaging parameters may be calculated from them. These comprise, for example, the climatic conditions of the packaging line, hold times for desiccants and product, etc. One constraint for calculating the suitability parameter 1 or its components may be the absolute quantity of water inside the package V.

The parameter 2 of the packaging system 6 or the SynPD model 15 is preferably used to calculate an absolute quantity of water or relative humidity within a packaged volume at the time of packaging. For this purpose, preferably the quantity of water in the substance 3 in the volume which is to be packed, the water content of the material packed together with the substance 3, particularly air, protective gas or the like and/or the moisture contained in the material of the packaging system 2 or packaging material are taken into consideration, particularly added, or used to determine a relative humidity, particularly by calculation. The amounts of water contained in the material of the package V and optionally causing a moisture ingress are particularly preferably calculated or determined by means of the sorption data 14 or sorption isotherms.

The packaged total volume and the quantity of moisture/water contained therein are preferably used to calculate the ambient conditions 5, be they stable or variable as a result of the permeation of the packaging, that can be expected for the substance 3 in the packaged state.

By means of the stability indicator 4, the stability of the substance 3 in the packaged state or the suitability indicator 1 is preferably calculated using the information relating to the ambient conditions for the substance 3 inside the packaging.

In order to verify the stability indicator 4, the parameter or parameters 6 of the packaging system 2 and/or the SynPD model 15, it is preferable if random samples of the substance 3 packaged using the packaging system 2 are exposed to certain ambient conditions 5 and, after a period of time, checked by measurement to see whether the calculated physical and/or chemical properties of the substance 14 correspond to the properties calculated using the suitability indicator 1. Alternatively, the SynPD model 15 and/or the parameter or parameters 6 may comprise correction values, particularly correction factors or the like, by means of which the calculation of the suitability indicator 1 can be better adapted to the actual circumstances.

The parameter or parameters 6 of the packaging system 2 is or are preferably permanently stored or held in a packaging database 12. The packaging database 12 preferably comprises parameters 6 for a number of different packaging systems 2. The parameter or parameters 6 of the packaging system 2 are preferably independent of the substance 3 which is to be packaged using the packaging system 2. This advantageously does away with the need to determine the parameter or parameters 6 afresh each time for determining the suitability indicator 1 for different substances 3. This facilitates and speeds up the identification of the packaging system 2 which is suitable for the substance 3.

FIG. 4 shows a package V of a proposed packaging system 2. In the embodiment shown it is a blister pack, particularly for tablets, capsules or other dry compacted materials.

The package V may comprise a receptacle 16 for holding the substance 3, particularly the tablets. The receptacle 16 may be a plastic blister, a bottle or the like. The receptacle 16 preferably comprises holders, recesses, indentations or other volume-forming devices 14. The receptacle 16 is shown in FIG. 5 from a different direction, which makes it easier to see the volume-forming devices 17, preferably for holding tablets, capsules or other substance 3.

The package V preferably comprises a closure means 18 which is configured to close off the volume-forming devices 17, preferably hermetically, or in airtight or gastight manner. For this purpose the closure means 18 may be glued, welded or otherwise tightly sealed to the receptacle 16. In the embodiment shown in FIG. 4, the volume-forming devices 17 are closed off by the closure means 18, apart from at the top left-hand corner of the package V.

As a result, in the packaging system 2, the ingress of moisture into package V is dependent on the permeation properties and sorption properties of the receptacle 16 and the closure device 15 in the region of the volume-forming devices 17. The permeation properties and the sorption properties immediately adjacent to the volume closed off by the packaging are particularly crucial.

The parameter or parameters 6 of the packaging system 2 is or are preferably determined by the packaging material which forms the package V, taking account of the permeation data 13 and sorption data 14. In the present case it is preferable if the moisture permeability and the moisture storability of the different materials involved in the package V are determined, particularly as parameter 6. For this, corresponding permeation tests and/or sorption tests may be carried out on the materials, as indicated, for example, by the arrow T in FIGS. 4 to 6. These tests may be carried out both on the individual materials and on a package V which has not been filled or contains only a dummy. The parameter or parameters 6 of the packaging system 2 can then be determined from the results.

It will be understood that different methods can be used for different packaging systems 2 in order to determine their adsorption or permeation data. These are known to the skilled man and therefore require no further explanation.

However, it is preferable if the sorption and permeation data or the parameters 6 associated with different packaging systems 2 are determined so that they can be compared with one another. For example, the parameter or parameters 6 may contain information relating to the particular individual packaging volume. This may be much larger in the case of a bottle than in a blister pack. When dry compacted material is packed into bottles, however, normally a plurality of discrete units of the substance 3 are packed simultaneously. Here, too, it is advantageously possible to calculate the suitability indicator 1.

If the packaging volume forms part of the parameter or parameters 6, the number of discrete units or the total volume of the substance 3 which can be packaged using the specific packaging system 2 can be determined automatically. The suitability indicator 1 can then take account of the fact that a plurality of discrete units of the substance 3, i.e. in particular, a plurality of tablets or the like, can be packaged in the same volume in a packaging system of a correspondingly larger volume.

The starting premise is preferably that even where a plurality of discrete units of the substance 3 are arranged in a shared volume or such an arrangement is calculated, the same spatial shape of substance 3 is present as in other packaging systems 2. Thus, a plurality of tablets or the like can be packed in a bottle. The overall larger total volume and the larger surface area etc. of the substance 3 is then preferably taken into consideration when calculating the suitability indicator 1.

The proposed method may then comprise a step in which the volumes, amounts or numbers of discrete units of the substance 3 that can be packed using the packaging system 2 are determined. This can then be taken into consideration when calculating the suitability indicator 1.

According to another aspect of the present invention which can also be implemented independently, after the stability indicator 4 has been determined, the suitability indicator 1 for different packaging systems 2 is calculated.

In order to calculate the suitability indicator 1 for different packaging systems 2, the stability indicator 4 may be mathematically linked to parameters 6 of the different packaging systems 2. As a result, a suitability indicator 1 can be calculated for a specific substance 3 in a specific presentation form for different packaging systems 2.

Different suitability indicators 1 which correspond to the same substance 3 in conjunction with different packages V or packaging systems 2 can then be compared with one another. Such a comparison can be undertaken in respect of different criteria. The suitability indicator 1 may, for example, comprise values which may correspond to shelf life, packaging labor, packaging costs or the like. Preferably, the suitability indicator 1 is compared with pre-existing data. For example, packaging systems 2 which do not meet a given durability criterion are automatically discarded. Alternatively or additionally, suitability indicators 1 of different packaging systems 2 are compared with one another. Comparisons may be made in respect of one or more values of the suitability indicator and/or by weighting different values of the suitability indicator 1.

The suitability indicator 1 may comprise one or more values which correspond to a reduction in active substance in the substance 3 or medicament. Such a reduction may be calculated on the basis of the stability indicator 4 and the relevant parameter 6. If the loss of active substance within a certain period of time is greater than a freely pre-determinable threshold, taking account of the results, corresponding packaging systems 2 may be automatically discarded. This can also be done with regard to other parameters, for example if a packaging system does not meet criteria with regard to the packaging labor, the packaging costs or the like.

A comparison module of the system S, not shown here, may be configured to calculate the corresponding suitability indicators 1 of different packaging systems 2 and to discard those packaging systems 2 which do not meet certain pre-defined minimum criteria. In one scenario, described by way of example, a precondition may state that, under certain ambient conditions, the loss of active substance must be less than a certain percentage, for example 4%, during storage over a period of time, for example 1 year. In an automated comparison, after the suitability indicators 1 for different packaging systems 2 have been determined, those packaging systems 2 in which the suitability indicator 1 has shown that this criterion cannot be met with the specific packaging system 2 are discarded. Alternatively or additionally, the comparison module is configured to display, store and/or label potentially suitable packaging systems.

According to another aspect of the present invention which can also be implemented independently, when mathematically linking 7 the stability indicator 4 to the parameter 6 and/or when determining the parameter or parameters 6 of the packaging system 2, the ambient conditions or climatic conditions under which the package V or the substance 3 packed in the packaging system 2 is exposed, particularly in practice, globally, climatically or in terms of sales operations, are taken into consideration.

The parameter or parameters 6 and/or the suitability indicator 1 may take account of, or depend on, the conditions or the part of the world, the temperature fluctuations or the average temperatures or the like under which the substance 3 packed using the packaging system 2 is to be stored.

According to another aspect of the present invention, the calculation of the suitability indicator 1 takes account of the interaction of the substance with the packaging system 2, particularly the product (substance 3) and package V, whilst underlying sets of data relating to the behavior of the package V or packaging system 2 on the one hand, and relating to the stability of the product (the substance 3), on the other hand, can be collected independently of one another.

The substance 3 in the sense of the present invention is preferably characterized both by its composition or formulation and by its specific presentation form. The stability indicator 4 or the stability indicator values 11 thus preferably take account of both chemical and physical properties of the substance 3, particularly including its presentation form, tablet size, coating, powder form, particle size, individual volume, surface area, ratio of surface area to volume, etc.

According to another aspect of the present invention which can also be implemented independently, the stability indicator 4 also takes account of non-linear behaviors/dependencies of the substance 3 during storage/open storage, particularly any degradation of the substance 3 which is not linearly correlated to the relative humidity or the water content of the substance 3. It may be envisaged that stability indicator values 11 are determined, in the manner described previously, and after they have been determined they are extrapolated and/or interpolated to characteristic curves or a characteristic curve set. In particular, the stability characteristics of the substance 3 are approximated by one or more polynomials and/or stored or taken into consideration in the stability indicator 4. The stability indicator 4 may thus comprise one or more characteristic curves or sets of characteristic curves.

In another aspect of the present invention, an infrared measuring device is used to determine the absolute or relative humidity or water content of the substance 3 and/or of the packaging material of the packaging system 2. Preferably, the infrared measuring device comprises an integrated conditioning cell and/or is used in a measuring mode of diffuse reflection. It has been found that the moisture content of the substance 3 and/or of the materials used in the packaging system 2 can be determined very accurately by this method. This contributes to accurate prognosis of the suitability of a packaging system 2 for packing the substance 3 or improves the accuracy of the suitability indicator 1.

According to another aspect of the present invention which can also be implemented independently, pure packaging data, particularly the initial moisture content and/or permeation of the package V or of the packaging system 2, and pure product data or properties of the substance 3, particularly stability in open storage are collected under product-specific climatic conditions, in particular, and/or taking account of product specific sorption data 14 or sorption isotherms.

Sorption data 15 or sorption isotherms can be collected and/or used for the substance 3 and/or the packaging system 2. Thus, it is possible for adsorption data 14 of the substance 3 to influence the stability indicator 4 or form part of the stability indicator 4. Alternatively or additionally, sorption data 14 and/or permeation data 13 for the packaging system 2, the package V or the materials used here may be taken into account for the parameter 6 of the packaging system 2 or may form part of the parameter or parameters 6 of the packaging system 2.

Particularly preferably, pure packaging data (parameter 6) on the one hand and pure product data (stability indicator 4) on the other hand are linked by a mathematical concept (permeation model/SynPD model 15). In this way it is advantageously possible to calculate a priori the relative humidity and particularly the product stability in one or more different packaging configurations or the substance 3 when packaged using different packaging systems 2.

According to another aspect of the present invention which may also be implemented independently, a package V or a packaging system 2 for a product or a substance 3 is or are identified and/or modified on the basis of the product stability or the suitability indicator 1 calculated. It is thus possible for a theoretically suitable packaging system category to be identified and adapted, particularly automatically, to the substance 3 or its dimensions.

According to another aspect of the present invention it is preferable if unsuitable packaging configurations are excluded right from the outset. In particular, for this purpose, the suitability indicator 1 is wholly or partially compared with one or more evaluation criteria or requirements and those packaging systems 2 which do not meet the corresponding criteria are discarded. In particular, a packaging system 2 for use with a substance 3 is discarded if it can be inferred from the suitability indicator 1 calculated in the proposed manner that one or more conditions for the stability of the substance 3 when packaged using the packaging material 2 are not achieved or maintained.

The present invention has been described primarily with reference to the effects of temperature and the absolute or relative humidity or the water content in the packaging or the like. However, alternatively or additionally, other influences such as UV light, the effect of air or air constituents or the like may be taken into consideration. It is possible, for example, for the stability indicator 4 or the parameter or parameters 6 to take account of the incidence of light, particularly UV light, other radiation and/or the diffusion of oxygen or other components of the air and/or of solvents like alcohol or the like in or through the package V. Measurements and/or stability indicator values 11 relating to these are preferably also carried out/determined as described and/or under otherwise constant ambient conditions 5 and/or for different periods of time over which the substance 3 is exposed to the ambient conditions 5.

According to another aspect of the present invention which can also be implemented independently, a weighting and/or selection of stability indicator values 11 that are to be determined and/or a weighting with mathematical linkage of the respective stability indicator values 11 and/or parameters 6 is or are carried out using the physical and/or chemical properties of the substance, particularly its sensitivity to light, moisture, temperature or the like.

Alternatively or additionally, weighting may be carried out when automatically selecting potentially suitable packaging systems 2 and/or when automatically discarding unsuitable packaging systems 2 as a function of the properties of the substance 3, particularly its sensitivity to moisture, temperature, UV light or the like.

For example, in the case of a substance 3 which is sensitive to changes in temperature or UV light, but which, being a solution, is substantially independent of relative humidity, a stability indicator 4, a mathematical linkage 7 and/or a comparison of suitability indicators 1 may also be carried out, even without taking account of the results in respect of relative humidity, and/or by reducing the consideration of these results by weighting.

According to another aspect of the present invention, in order to determine the parameter or parameters 6, information as to the atmosphere under which packaging is carried out is taken into account. Regarding the packaging system 2, besides the materials and structure of the package V, the packaging process as such may also be taken into consideration. For example, elevated temperatures or the like may occur during the packaging process. This tends to occur more in the ultrasound welding and/or sealing of blisters than in the tightening of a screw top on a bottle. The parameter or parameters 6 of the packaging system may take account of or include properties of the packaging process associated with the packaging system 2.

The permeation data 13 of the package V, the sorption data 14 or sorption isotherms of the package V and/or the open storage data and/or permeation data and/or the sorption data or sorption isotherms of the substance 3 are preferably determined experimentally. Alternatively or additionally, the sorption data or sorption isotherms can be determines automatically, e.g. by a (database) look-up or the like.

The permeation data 13 of the package V and/or the sorption isotherms which can be produced by DVS measurements preferably flow into the permeation model/the parameter 6/the SynPD model 15 of the packaging system 2. In particular, a permeation model SynPD model 15 or one or more parameters 6 of the packaging system 2 is or are calculated from the permeation data 13 and sorption isotherms. It is thus preferable if permeation data 13 and sorption data 14 are mathematically linked to one another or calculated, extrapolated or interpolated with one another in order to determine the permeation model or the parameter or parameters 6 of the packaging system 2.

In one embodiment of the present invention, the breaking strength of the substance 3, the disintegration time of the substance 3 and/or the release of active substance or its conversion into or out of the substance 3 are taken into consideration for or by the stability indicator 4 and/or for the parameter or parameters 6 of the packaging system 2 and/or for the SynPD model 15.

With regard to the parameter 6 it is preferable if adsorption and permeation rates are collected for the materials used, from which the moisture balance and the ingress of moisture into the package per unit of time can be calculated over a certain length of time, particularly over the whole period, particularly as parameter 6. The data can be determined from Mocon measurements or permeation measurements of a deep drawn packaging material or indirectly by evaluating DVS results. Corresponding measurements or results are preferably additionally verified by permeation experiments on packaging.

According to another aspect of the present invention the water content in the substance 3 and in the package V or packaging material is determined at least in the region of a section thereof which forms a receptacle or chamber for the substance 3, which is or are present at the time of packaging. The sorption isotherms are preferably taken into consideration or are contained in the parameter or parameters 6 and/or the stability indicator 4.

With the sorption isotherms of the substance 3 and/or the packaging material, at least in the sections immediately surrounding the substance 3 in the packaged state, the initial moisture content of the system as a whole is preferably determined. On the basis of the initial moisture content of the system as a whole, i.e. the sum of the moisture or water volume of the relevant section of the packaging and the moisture contained in the substance 3, a development over time for the environment formed in the packaging or a development over time for the ambient conditions surrounding the substance 3 in the packaging is preferably calculated. The results can be used to calculate the suitability indicator 1 by means of the stability indicator 4.

In one aspect of the present invention, only the overall model or SynPD model 15 is produced, without calculating the suitability indicator 1.

In another aspect of the present invention which can also be implemented independently, (only) the stability indicator 4 is determined, the stability indicator 4 preferably comprising physical parameters and chemical parameters.

In another aspect of the present invention which can also be implemented independently, (only) the stability indicator 4 is determined, the stability indicator 4 comprising physical and/or chemical parameters and sorption data and/or permeation data relating to the substance 3.

According to another aspect of the present invention, the number of measurements for determining the stability indicator 4 and/or the parameter or parameters 6 is dependent on the degree of change in the respective results. Preferably, the time interval between measurements or characterizations of the substance 3, particularly during open storage, is reduced if an increased rate of change has been ascertained by (the previous) measurements.

According to another aspect of the present invention, the measurements are examined in connection with the determination of the stability indicator 4 or parameter 6 in respect of particular isothermic forms and/or the formation of characteristic hysteresis. Depending on these, the number of measurements of the substance 3 can be altered or determined.

According to another aspect of the present invention, sections of the sorption isotherms of the package V or of the substance 3 are analyzed for a sudden significant uptake or release of water. If such a sudden significant uptake and/or release of water is detected, which goes beyond the uptake or release of water in other areas in absolute or percentage terms, critical areas can be detected and/or thresholds can be (automatically) fixed, particularly for the evaluation or comparison of packaging systems 2 or suitability indicators 1.

According to another aspect of the present invention, regions of phase transitions in the sorption and/or desorption cycle are incorporated in a controlled manner and closely analyzed. In particular, in this region, variations between corresponding samples which are smaller in terms of the storage time and/or storage moisture content and/or storage temperature, particularly in the open storage study, at short time intervals or smaller changes in relation to temperature and/or absolute or relative humidity, are used to determine the stability indicator 4 by comparison with other regions.

Generally, it is preferable if samples of the substance 3 are taken at short time intervals when a parameter is varying sharply during the open storage study, but are taken increasingly less often as the values stabilize. A small distribution and a high information density as values vary have proved advantageous for the accuracy of the subsequent simulation computation.

According to another aspect of the present invention, the characteristics, particularly stability characteristics, of the substance 3 packaged using the packaging system 2 are simulated and preferably open storage data are calculated with package-specific data.

Further aspects of the present invention are explained in more detail hereinafter, the term substance 3 and the term "product" being used synonymously. Where reference is made hereinafter to a "product", the term product or preparation may also be replaced by the term substance 3 or vice versa.

In the following description the substance 3 or an extract from the substance 3 is referred to as a sample which is taken or prepared for analytical purposes. The term "sample" can therefore also be replaced by the term "substance 3".

According to another aspect of the present invention, results of analysis, particularly during the open storage study and/or at 25° C., are considered independently of the storage humidity, so that the effect of the relative humidity alone on the product properties at constant temperature is detectable. In addition, tendencies and critical areas can be identified early and monitored with greater attention. Thus, as a consequence, intervals, both of time and temperature, moisture and/or UV light or the like can be narrowed down.

According to another aspect of the present invention a characterization of stability properties of the substance 3 or the determination of stability indicator values 11 for the substance 3 can be stopped as soon as unacceptable parameter values/stability indicator values 11 for the product/substance 3 are obtained repeatedly with certain humidity series. Then the continuation of the sample analysis towards higher moisture levels can be stopped and advantageously avoided. In such cases the stability indicator 4 preferably comprises values which correspond to the substance 3 being unsuitable for corresponding moisture conditions. Alternatively or additionally, stability indicator values 11 may be set at a threshold value or an extreme value.

According to one aspect of the prevent invention, the exclusive effect of the temperature alone on the product can be observed on samples which have been dried to the maximum, i.e. at a storage humidity of less than 1% relative humidity at the temperature in question. Under these conditions the product has an extremely low, virtually negligible water content, so that changes in the parameters of the two samples (separately) under otherwise constant conditions can only be put down to a variation in the temperature.

To enable the influence of the temperature to be investigated when there is moisture present in the product at the same time, it is preferable to maintain a constant water content in the samples so as to vary only the temperature parameter. This takes account of the finding that the number of water molecules directly available as potential reactants in the sample is crucial to the stability of an active substance or product. Therefore it is assumed that if the number of water molecules remains constant it is possible to make a definite statement as to the effect of varying temperature conditions on the product.

Generally, it is desired and appreciated to keep any condition that might result in a stability variation of substance 3 constant apart from that to be investigated. In particular, any solvent content or concentration can be kept constant similar to the procedure described with regard to water/humidity. With regard to investigation of UV-influence, any temperature variation resulting from absorption of radiation can be compensated for by adapting the ambient temperature and/or by ambient atmosphere movement. This enables investigation of the influence of different potentially stability effecting conditions independently of one another. These can be used for or as the stability indicator and/or its stability indicator values.

According to one aspect of the present invention, using sorption isotherms at the respective temperature, the precise relative humidity at which the water content in the product does not change by comparison with a reference temperature, particularly 25° C., is selected. Thus it is particularly preferable that the relative humidity of the environment 5 should be changed, when the temperature is changed in connection with the characterization of the substance 3 or the determination of the stability indicator 4, so that the absolute water content or the number of water molecules in the sample or substance 3 is kept constant. Preferably, relative humidities corresponding to one another while a constant water content is maintained in the product or in the substance 3 are determined particularly by means of sorption isotherms. Preferably, starting from a sorption curve or sorption isotherm corresponding to a first temperature, a relative humidity corresponding to a constant water content at both temperatures is determined.

It is preferable that the relative humidity of the environment 5 is increased as the temperature is increased in order to maintain a constant water content in the substance 3. Besides the described method of determining the changed relative humidity, other methods may also be used.

According to one aspect of the present invention, values corresponding to one another or associated with one another, particularly in terms of the humidity, the parameter or parameters 6 of the packaging system 2 and the stability indicator 4, are linked together, preferably in order to determine the suitability indicator 1, particularly by computation.

The stability indicator 4 and/or the suitability indicator 1 preferably comprise or comprises one or more values corresponding to the following properties of the substance 3: effects of hydrolysis, effects of redox reactions, effects of steric rearrangements, formation of polymorphs, formation of amorphous crystalline transitions, formation of hydrates, breaking force, hardness, friability, disintegration, solubility, speed of dissolving, release characteristics, swelling, swellability, color, odor, flavor, enzymatic breakdown, mould attack.

Preferably, in order to determine the stability indicator 4, the water content, hereinafter also referred to as the product humidity, of the substance 3, hereinafter also referred to as the product, is measured.

The product humidity can be quantified using numerous direct and indirect methods of measurement. The direct methods include all the methods linked with re-weighing or initial weight, i.e. all the (thermo-) gravimetric methods of measurement as well as Karl Fischer titration. They are used as reference methods for calibrating indirect water measurement methods. In the indirect methods of measurement, either analysis is carried out as to how physical properties of a material change as a function of the water content, or how the water molecules contained in the sample react to a physical stimulus. The individual methods of measurement differ in their speed, accuracy and detection limits, their sample requirements, their complexity and their risk potential, e.g. on account of the chemicals needed.

The term sorption preferably encompasses all the processes in which molecules either accumulate on interfaces (adsorption) or are adsorbed directly into the volume of another phase (absorption). The material which accumulates or adsorbs other molecules is referred to as an (ad/ab)sorbent or (ad/ab)sorption agent. Until sorption occurs the molecules are referred to as sorptive and thereafter as adsorpt/absorpt or adsorbate/absorbate. In addition, a distinction is made between physisorption and chemisorption. In physisorption, physical bonds exist between the sorbent and the sorptive, such as for example electrostatic interactions, dipole-dipole interactions or Van der Waals forces. In chemisorption, on the other hand, chemical bonds are usually formed under the influence of higher temperatures, thus making the following reactions possible for the first time (catalyst principle). If one looks particularly at the concentration of water molecules, this is a physical adsorption or absorption, depending on the nature of the sorbent. Depending on the relative humidity, the water molecules may be adsorbed onto surfaces either as mono- or multilayer coatings, or taken up as individual molecules or in water clusters by an absorbent. From the resulting pattern of the sorption isotherms, conclusions can be drawn as to what type of sorption characteristics are present in all probability. If hysteresis occurs, it can be assumed that a porous sorption agent was present, the pore size of which can be determined more accurately by means of the shape of the sorption isotherms. The pore diameters are classified according to IUPAC.

The permeation P is generally defined as a process in which a substance migrates through a solid. In the first step, sorption of the substance takes place, followed by diffusion through the solid until the substance is desorbed on the other side of the material. The permeation co-efficient also refers to the substance constant of a material which, in the case of water vapor, is defined as the amount of water which permeates through a sample with a standardized area and known layer thickness within a specified period of time. It always relates to the temperature selected and the moisture gradient present during the measurement as well as the ambient pressure.

$$P_{[T,\Delta r.h.]} = \frac{\text{Amount of water} \cdot \text{layer thickness of the sample}}{\text{Unit of time} \cdot \text{sample area}} \left[\frac{g \cdot mm}{d \cdot m^2}\right]$$

With the permeation rate, on the other hand, the vapor permeability is based on a specific examined object and given as a quantity of water exchanged per day (g/d). It quantifies the permeation for a specific sample, i.e. for a fixed sample dimension and layer thickness/wall thickness under the prevailing measuring conditions such as temperature, relative humidity and air pressure. The permeation rate allows a direct comparison to be made between theoretical and experimental permeation values of a sample, and comparison within a set of similar samples. It is particularly advantageous to use an experimentally determined permeation rate when there are no uniform wall thicknesses or layer thicknesses because of the manufacturing process of the packaging material, meaning that calculation of the permeation rate would lead to unacceptable errors, or on the other hand, for a theoretical estimate, the area sizes of difficult geometric shapes would have to be determined.

The vapor permeation into a blister is chiefly determined by the nature and thickness of the film material. However, on detailed observation, further factors influencing the permeation rate can be identified, such as for example the dimensions of the blister cavity, the width of the sealing edge, the nature of the seal and the sealing parameters set such as temperature, sealing pressure and time. In the case of an aluminum blister which is, of itself, very well sealed, it should also be borne in mind that a certain amount of moisture enters the cavity through the adhesive layer between the top film and bottom film or through the seal. In other blister materials this aspect is completely irrelevant to the moisture balance in the well and can therefore be ignored in any calculations.

The permeation rate P or permeation coefficient P of vapor through a particular material can also be calculated if the diffusion coefficient (Dw) and the saturation solubility (S) of the water in the material are known. The following physical correlation applies:

$$P(r.h.,T) = D_w(r.h.,T) \cdot S(r.h.,T)$$

wherein:
P is the permeation rate
Dw is the diffusion co-efficient
S is the saturation solubility
r.h. is the relative humidity and
T is the temperature.

The equation particularly takes account of a possible moisture dependency of the permeation rate or the permeation co-efficient. It is used to determine, by means of DVS measurements, the permeation rate and activation energies for sorption and possible diffusion as well as permeation.

The hitherto traditional procedure in product and packaging development is based on the methods demanded by the licensing authority. Formulations/products are typically tested for stability in different packaging configurations under different climatic conditions. The suitable packaging is determined using the results of these stability studies, i.e. by trial and error. In particular, in the purely traditional approach, the relative humidity and indeed the stability of the product in a package cannot be determined beforehand but is ascertained over the course of the stability study, i.e. only after a corresponding time delay.

By contrast, in the SynPD concept, i.e. using the SynPD model according to the present invention, proposed here, a completely new approach is taken. Pure packaging data (initial moisture content, permeation) and pure product data (stability in open storage under product-specifically selected climatic conditions, sorption isotherms) are collected and linked by a mathematical concept. In this way it is possible to calculate a priori the relative humidity and particularly the product stability in any desired packaging configuration. On the basis of these results, the best possible packaging tailored to the product is identified and the subsequent packaging stability testing is limited to the candidate or candidates. Unsuitable packaging configurations are thus excluded right away. Furthermore, critical stability areas are also identified beforehand by the SynPD concept. Alternatively or additionally, SynPD concept enables adapting the packaging concept such that regions or areas which are particularly relevant or critical with regard to stability can be avoided. In particular, a suitable packaging material (foil) can be chosen, the geometry of a blister can be adapted, the substance 3 can be pre-conditioned (e.g. dried), and/or the packaging material can be pre-conditioned (e.g., dried), in particular prior to performing the packaging process with it.

According to the present invention, pre-condition of substance 3 and/or of the respective packaging material can be considered for determining the stability indicator 1 and/or a suitable packaging system.

With the present invention the reaction of the product to external influences such as, for example, relative humidity, temperature or UV light can be unambiguously calculated analytically by means of the change in chemical and, especially, physical product properties as a function of the operating time. As a product's individual "fingerprint" is collected with the open storage data, the calculations require neither approximation solutions nor assumptions of functional parameter correlations. SynPD was deliberately developed as a generalized mathematical/physical procedure to be very widely applicable, i.e. theoretically to all stability parameters the influencing factors of which are known. The stability data for the product calculated beforehand using SynPD offer a high information content by means of which manufacturing and packaging processes and handling times in operation can be optimized, but also storage conditions and in-use times can be determined beforehand. As a result, a preparation developed by this method can only lead to more advantageous development times or minimized development risk for the pharmaceutical manufacturer and increased safety for the user.

The data required for the SynPD modeling of the product stability and the computing operations carried out are described in detail in FIG. 3 and their theoretical background is explained more fully in the following paragraphs.

The experimentally collected values are, in particular, open storage data as well as permeation data 13 and sorption isotherms 14 or sorption data which are preferably determined by dynamic vapor sorption (DVS) of the product.

Dynamic vapor sorption is particularly suitable for determining the stoichiometric molar ratio between water and substance. On the one hand, the humidity stages at which hydration or dehydration occurs can be determined precisely and on the other hand the quantities of water thus exchanged can be determined precisely to the nearest microgram. At the same time, information is obtained regarding the kinetic trend at the critical relative humidity. Moreover, it can be inferred from the sorption isotherms 14 of the substance investigated whether the formation of higher-valency hydrates takes place gradually or in one step.

A fundamental difference from the methods used hitherto is that all the influencing factors which in the last analysis share responsibility for the product stability are analytically characterized separately from one another in the accurate detail required. In this way the maximum information content on each individual component is acquired, uncontaminated by influence from other components. The advantage of this approach is that weaknesses in the overall system can be identified early and improved, thus saving time and expense in an ongoing project.

The three data blocks which can be experimentally collected and on the basis of which the subsequent modeling is preferably carried out are described in more detail hereinafter.

Preferably, open storage data for the product are determined, preferably measured, for which in general, all the product properties critical to stability, or a selection of them, can be used. Further criteria for the suitability of individual product parameters for the SynPD computer simulation are, firstly, the most accurate measurability possible and, secondly, the dependency on other external parameters such as, for example, relative humidity, temperature, UV light, oxygen (concentration and/or absorption) and/or solvent (concentration and/or absorption).

For SynPD modeling, it is particularly preferable to examine the two physical parameters of breaking force and disintegration time and the chemical parameter of the release of active substance. In contrast to conventional stability studies, the generation of stability data is preferably not carried out either in the primary packaging or at fixed intervals of time but according to a completely different plan. The open storage concept is illustrated by way of example in the Table in FIG. 2.

Preferably, for the packaging materials used, sorption and permeation rates are collected from which the moisture balance and the moisture ingress per unit of time into the packaging can be calculated over the entire running time. The data can be obtained directly from Mocon measurements or indirectly by evaluating DVS results and are preferably additionally supported by permeation experiments on packaging. The permeation rates obtained are preferably fed into SynPD model calculations for product stability.

Preferably, the sorption and desorption properties of packaging components and products are used, which can also be determined using DVS measurements. Using the sorption isotherms the water content in both components which is present at the time of packaging is determined. The moisture ingress through product and packaging is crucially responsible for the initial moisture content of the system as a whole.

In particular, the model computation, for example on a bottle, with desiccant, incorporates the sorption isotherms of the product, of the bottle material, of the desiccant and of the air contained in the bottle. In the case of blisters, it is preferably the sorption isotherms of the top and bottom films, the hot melt adhesive, the air in the blister, the product, or the substance 3 (which in turn may consist of different components).

A range of more extensive information is particularly preferably inferred from the development of the sorption curves, especially in addition to the sorption capacity and the sorption kinetics of the materials investigated. In particular, using the isotherm shape and the development of characteristic hysteresis, conclusions are drawn as to the nature of the incorporated water and are preferably taken into consideration or used in the determination of the stability indicator 4, the parameters 6 and/or the suitability indicator 1.

Noticeable points in the sorption isotherms 14 which are connected to a sudden sharp uptake or release of water possibly indicate critical relative humidities for the product. In these areas it is advisable to monitor various product properties carefully, and this in turn plays a crucial role in the choice of storage humidities when carrying out the open storage studies. Such information is preferably also taken into account or used when determining the stability indicator 4, the parameters 6 and/or the suitability indicator 1.

In contrast to stability studies carried out in the conventional manner the product is subjected to an open storage study in the procedure according to the SynPD concept. By this is meant that the loose product is stored open under selected defined climatic conditions so that in analyses it is possible to determine the direct reaction of the material to the climate provided, unimpeded by packaging.

In this way a fingerprint of the pure product properties is obtained, which is completely uninfluenced by any packaging. However, this does not rule out the possibility of information regarding the compatibility between the product and different packaging materials being additional obtained during the test procedure, if necessary.

Moreover, in contract to traditional stability tests, the open storage concept is preferably structured so that the influence of relative humidity or water content and temperature can be investigated independently of one another.

First of all, at 25° C., for example, in addition to very dry and moist extreme conditions, other storage humidities are selected which are determined individually for each product by means of the sorption isotherms (see the first line in FIG. 2). Ideally, all the critical ranges such as, for example, phase transitions in the sorption and desorption cycle, are covered so that product is deliberately stored and subjected to analysis below and above a noticeable moisture stage.

In principle, all the chemical and also physical product properties which can be determined by measurement with sufficient accuracy, precision and robustness and which are dependent on external influences such as climate or UV light or oxygen concentration are suitable as measuring parameters for the later SynPD modeling.

The times for the sampling are selected dynamically according to the product properties (cf. the penultimate line in FIG. 2). If a parameter changes significantly, samples are taken at short intervals, whereas when values are stabilizing samples are taken less and less frequently.

It should be borne in mind that the later computer models are based on these data, so that a small distribution and a high information density in the case of varying values have proved advantageous for the accuracy of the subsequent simulation computation. If the results of the analysis at 25° C. are looked at as a function of their storage moisture content, the influence of relative humidity alone on the product properties at constant temperature becomes detectable. At the same time, tendencies and critical areas are identified early and can be monitored with greater attention. As soon as unacceptable parameter values are repeatedly obtained for the product in certain humidity series, their continuation in the sample analysis can be stopped, with the result that the creation of these moisture conditions should be avoided later by the choice of suitable packaging materials.

According to one aspect of the present invention, the effect of the temperature on the product parameters should additionally be investigated. A temperature of 40° C. appears to be a suitable choice as the authorities in any case require stress stability at 40° C./75% r.h. The exclusive effect of the temperature alone on the product can be observed on samples which have been dried to the maximum, i.e. at a storage humidity content of less than 1% r.h. at the temperature in question (second column in FIG. 2, arrow). Under these conditions, the product has an extremely low, virtually negligible water content, with the result that changes in the parameter in the samples, with all other conditions remaining constant, can only be put down to a variation in the temperature (in this case from 25° C. to 40° C. or vice versa).

In order to be able to examine the influence of the temperature whilst moisture is simultaneously present in the product, the water content in the samples is preferably kept constant so that only the temperature parameter is varied (see FIG. 3, remarks in the second line). This allows for the finding that the number of water molecules directly available as potential reactants in the sample is crucial to the stability of an active substance or product. When the number of water molecules remains constant, therefore, definite pronouncements can be made as to the effect of changing temperature conditions on the product (see FIG. 2, marked by arrows).

By means of sorption isotherms, preferably from DVS measurements, the precise relative humidity at which the water content in the product at 40° C. does not change by comparison with 25° C. is selected. To achieve this, as shown in FIG. 7, starting from the 25° C. sorption curve, a line is drawn which is horizontal to the 40° C. curve (corresponding to a constant water content at both temperatures) and the relative humidity belonging to the intersection is read off on the x-axis. For example, at 40° C., instead of 40% relative humidity a relative humidity of 45% may be selected, or instead of 60% a relative humidity of 65% may be selected. Once the conversion and storage of the samples has been carried out for all the columns mentioned in FIG. 2, finally the interaction of humidity and temperature on the product at increasing water levels can be evaluated (comparison of the individual columns from left to right). This procedure can be applied to a different first and second temperature, and thus 25° C. may generally be the first temperature and 40° C. may be a second temperature.

Advantageously, when stored open, the product immediately comes into contact with the certain relative humidity envisaged, so that the reaction to the loading can be observed instantly. It is thus possible to evaluate the product behavior for different climatic conditions or climatic regions at the same time, in order to define, even at this stage, first requirements of the later packaging configuration. However, if the product is tested for stability in packages of different permeability using the conventional approach, the achievement of a critical or damaging relative humidity is set at completely different times. Taking a critical humidity of 60% r.h. at 25° C. by way of example, in the PVC blister the period of time until this extreme humidity is reached is only a few days. In the PVC-PVdC blister this same moisture level is achieved after one month, in the triple layer PVC-PVdC-PVC blister it is achieved after 5 months and in the Aclar® blister it is only achieved after 10.5 months.

In the SynPD concept, the effects of temperature and humidity are preferably investigated separately from one another so that the deciding factor for the product stability can be clearly identified. For this purpose the temperature is kept constant to begin with and only the storage humidity is varied. Critical and optimum moisture ranges are characterized as well as relative humidities with development trends for a product parameter at an early stage. In a later step the interaction of the two influences is also examined. Only the temperature is varied, while the moisture content in the product is kept constant according to the sorption isotherms. It is thus possible to tell whether temperature fluctuations are tolerated by the product or become critical only as a function of certain water contents. Consequently it is possible to estimate from an early stage whether operation in all climatic zones is possible without any problems or whether additional measures have to be taken. By contrast, conventional storage according to climatic zones does not allow product analysis with a comparable high information content, as the two parameters, temperature and humidity, are varied simultaneously. Also, storage is only carried out under climatic conditions which are selected at individual points, so that the behavior of the product thereafter cannot be assessed except with difficulty and with limited reliability.

Another advantage of the SynPD concept is that the samplings are chosen for dynamic time intervals. As a result the critical times at which noticeable changes occur in the product are detected with great accuracy with a high data density. These product data are of interest for manufacture, sale, storage and in use as they provide valuable information as to the rate at which processes of change occur and what time windows are available accordingly. With rigidly fixed sampling at 3 monthly intervals according to the ICH Guideline Q1A and the WHO Guideline, it is not possible to achieve a comparable information content. If this sampling scheme were to be applied to the example, unacceptable damage would only be detected after 3 months' storage for the PVC and PVC-PVdC blister, but it would not be discovered that the product no longer met the specification within the first month.

Moreover, the stability calculation according to the SynPD concept provides reliable and authoritative results as the individual open storage data of the product are used and therefore there is no need for approximation or data extrapolation. The concept is also universally applicable to all measureable product parameters. Moreover, when the Arrhenius stress test is applied to product data collected at high temperatures this can be extrapolated to significantly lower storage temperatures. This procedure may be prone to errors and is only permissible, in particular, under certain preconditions, namely in exclusively thermally controlled chemical reactions. Other influencing factors have to be carefully excluded from the outset, as otherwise false assumptions will be made regarding the product stability.

The application of the SynPD concept in a project also has an advantageous cost-benefit ratio. Admittedly, the material and staff costs are initially higher and hence the cost at an early stage of the project, but on the basis of the information and data density relating to the product the further proceedings on the way to submission are optimally controlled. As the optimum packaging has already been decided before the start of a packaging stability study and unsuitable candidates can be reliably excluded, high-cost trial and error loops can be avoided at this stage of the project and the risk of time-critical reverses is significantly minimized. Experience has shown that this represents a cost of about 1.5 million US$ for each stability test.

The permeation model serves to simulate the moisture economy in a packaging system at the time of packing, during storage or during the life of the preparation and, particularly, while it is in use by the patient.

The setting up of the computer model requires on the one hand the experimentally obtained permeation data 13 which determine the ingress of moisture through the packaging at a defined time interval. Also included are the sorption isotherms 14 of the product, packaging and any desiccants, on whose sorption capacity the initial moisture content and further development of moisture depend. To simulate the development of the relative humidity which, in this example, is supposed to increase in the package during storage, the following procedure is adopted. It should be noted that the reverse moisture gradient could also be considered, as permeation is not restricted to one direction.

Preferably, in a first step, in order to calculate the suitability indicator 1, the initial moisture content or total amount of water available within the package V of the individual substance 3 is determined. In order to determine an initial moisture content in the package V, preferably the amounts of water in all n individual components is totaled:

$$r.h._{start} = \frac{\sum_{i=1}^{n} m_{i\ actual}(H_2O)}{\sum_{i=1}^{n} m_{i\ 100\%}(H_2O)} [\%] \text{ at } T\ [^{\circ}C.]$$

$$\text{where: } \sum_{i=1}^{n} m_{i\ start}(H_2O) = m_0$$

which are present at the time of packaging, depending on the particular packaging state. The water contents may be derived directly from the sorption isotherms of the materials if the storage humidity and temperature are known.

Individual components to be taken into consideration are preferably all the product components, all the packaging components such as the top and bottom films, pouches and optionally desiccants, and the quantity of water in the remaining volume of air in the blister cavity. The sum of the water actually present is divided by the sum of the maximum possible at 100% saturation, which gives as the result the relative humidity at the start of the packaging study. Alternatively or additionally an equation system with the non-linear sorption isotherms of the components is solved.

Preferably, particularly next, the moisture gradient present at the starting time $ti=0$ is determined from the difference in the storage humidity or the relative humidity surrounding the package V and the initial humidity present in the package. As function of these, the value of the permeation rate at $t0$ can then be calculated, which indicates the quantity of water $\Delta m$ which is transported through the present package during a fixed period of time $\Delta t$. The linear dependency of the permeation rate on the relative humidity as shown below has been confirmed by numerous measurements and is valid for all the film materials investigated thus far (for linear approximation, while non-linearities can be considered alternatively or additionally).

$$P = k \cdot \frac{r.h.[\%]_{outside} - r.h.[\%]_{inside,t_O}}{100} \left[\frac{\mu g}{\Delta t}\right]$$

wherein:
P=permeation rate at the moisture gradient currently present
k=permeation rate at a moisture gradient of 100%
$t_0$=starting time
r.h.=relative humidity The humidity $\Delta m$ registered during $\Delta t$ is distributed over all the absorbent components in the system as a whole in accordance with their sorption capacity, i.e. the product, packaging material, desiccant and the remaining air content in the cavity.

The new relative humidity at a constantly maintained temperature T at time $t0+\Delta t$ ($\Delta t$=time difference) is calculated finally by dividing ($m0+\Delta m$) by the maximum possible total quantity of water at 100% saturation. Using the moisture gradient currently present, the permeation ratio applicable to the time $t0+\Delta t$ can then be determined, thus starting a new computing cycle at the same time. The iterative computing loops are repeated until the observation period is achieved or until the entire system is in thermodynamic equilibrium with its external humidity.

The permeation model described is generally valid and can also be used, after suitable mathematical adaptation, with non-linear sorption isotherms or those extending exponentially or in steps. The iterative process used in the computation has the advantage that neither derived nor integral functions have to be found, which would be a very laborious process or even impossible with certain types of functions.

As is illustrated by way of example below, numerous questions regarding humidity and product stability can be answered in this way. Using the model 15 it is possible to calculate the initial moisture content of a packaged product, the ingress of moisture into the package per time period, the distribution of the permeated water over each absorbent individual component, particularly the water content of the product at each time and the development of the relative humidity throughout the system as a whole under the climatic conditions selected.

For example, the time taken to achieve total equilibration of a packaging configuration as a function of the storage humidity can be calculated in advance, or the time taken to reach a critical relative humidity for the product. Thus, even before the start of a packaging study, the types of blister that keep the product stable for the shelf life envisaged can be identified. As a result, only the pre-selected blisters are included in the subsequent stability investigations, thus saving on materials, staffing capacity and time.

At the same time, the simulation shows whether an expensive blister is strictly necessary or whether a cheaper variant with a higher permeability would still give adequate protection for the product. Moreover, using the model it is possible to decide what type of desiccant works most effectively and what size or oversizing is required and useful. If a product must not fall below a specified humidity limit, moisture-pretreated silica gel is included. In the model, it is possible to determine the packaging humidity at which silica gel does not dry the product too much but still has sufficient residual absorption capacity to stabilize the product throughout its shelf life within a defined humidity corridor.

Moreover, there is the possibility of calculating time scales for bulk goods packaging or repackaging processes. The latter is relevant, for example, in the event of a shutdown of machinery in production as the ambient humidity affects all the individual components for a corresponding period of time. Using the model computation it is possible to state to what extent the product, film materials or desiccants can still be used or whether they have to be discarded immediately.

The aim of the computer model is, in the last analysis, to protect a moisture-sensitive product to the optimum degree and to identify the best possible tailored packaging configuration quickly and unambiguously.

In the present invention, the ingress of moisture through the packaging material or packaging system 2 itself and/or the effect of changes in air pressure on the humidity, particularly in bottles, are taken into consideration, particularly when determining the stability indicator 4, the parameter or parameters 6 or the SynPD model 14.

In contrast to the permeation models published previously, SynPD simulation calculations are preferably not restricted to the modeling of the development of humidity in a package. Preferably, physical/chemical product properties in different packaging configurations are analytically precalculated and in this way the stability of the product is mathematically predicted in advance of packaging studies actually carried out.

The results of the permeation model for a blister of defined dimension are preferably calculated with product data from the open storage study.

According to an aspect of the present invention which can also be implemented independently, a hypersurface of the substance 3 is determined using the open storage test. Preferably, a variable corresponding to the stability of degradation of the substance 3 or the stability indicator 4 is represented, detected or interpreted as a function of an influencing factor, particularly the relative humidity or the temperature or both and/or some other ambient condition, and the storage time as a hypersurface.

The development of the influencing factor, particularly the relative humidity or the temperature or both and/or other ambient condition can be recorded, registered or taken into consideration as the pattern of the influencing factor over the storage time or time period or vice versa. By projecting this pattern onto the hypersurface the stability of the substance 3 or the suitability indicator can be determined. The present steps are carried out in a corresponding manner without any graphical representation.

By way of example, the decomposition of the active substance of a product is used, which has been exposed for example to different relative humidities between 10 and 60% r.h, for example, at 25° C. and preferably analyzed at defined time intervals according to the ICH or WHO Stability Guidelines.

In particular, pure packaging data with pure open storage data are calculated in order to predict the product stability.

The two data sets, parameter 6 and stability indicator 4, can be represented and/or extrapolated and/or interpolated for further processing in a three-dimensional form and/or as a hypersurface, in particular in order to be able to monitor the individual computing steps with a graphical illustration.

Particularly preferably, two-dimensional open storage data of the degree of decomposition are additionally fanned out, as a function of time, over a third axis, namely the relative humidity. These data need not be present in graphic form but may also be provided in the form of a table, matrix or the like.

Preferably, the pattern of the humidity development in the blister is determined, preferably by calculation.

In one step, the decomposition data are first fitted by means of a fitting function in order to smooth a non-physical sequence of measured values beforehand, such as, for example, an apparently lower proportion of decomposed active substance at a later measuring time. It should be borne in mind that the data fit with the smallest squares of the errors is not necessarily the best, e.g. a polynomial function of a higher order, but that the fitted curves primarily have to be physically/chemically reasonable. Interpolation with the method of the smallest squares of the errors is preferred, however.

The results of the smoothing are optionally entered, stored or incorporated in the diagram, table, file or database or the like or form a part of the stability indicator 4, the parameter 6, the SynPD model 14 and/or the suitability indicator 1.

Preferably, a matrix or hypersurface is calculated, particularly using the Renka-Cline gridding method which connects all the fitted curves to one another through a grid structure and describes the physically/chemically most reasonable correlation between the individual measurement series. For this purpose, an interpolation regarding different parameters may be provided, particularly using the temperature, humidity, time and/or other ambient conditions.

It is also preferable if fitted curves for the original measured values are derived or differentiated after the storage period.

In order to create a more meaningful database, additionally a suitable number of intermediate grid lines or interpolated points, lines or the like is selected or determined and/or also differentiated according to time. This procedure is permissible as, using the Renka-Cline gridding method chosen to generate the grid, curved patterns are calculated which are self-similar to the original data.

Preferably, the blister or other packaging determines, as a function of its permeation rate, what relative humidity is present in the packaging at a certain point in time. With a knowledge of the vapor concentration, in particular, the derived value present at this time is preferably obtained from the associated derived graph.

In the embodiment, a vapor concentration, for example 40% r.h. at 25° C., is present after about half a month. At the (0.5 month) value in the derivation graph (of the 40% r.h. measuring series) a derived value for the decomposition can then be read off. The same procedure is used for other relative humidity where once again a derived value is associated with the corresponding times using the time/humidity profile of the blister.

This new (graphical) pattern thus obtained is subsequently integrated according to time and added to the initial value of the investigation parameter under consideration. The resulting curve represents the partial integral according to time, mathematically $\int (\partial h / \partial t) \, \delta t$.

Analogously to the graphically based process described here, the decomposition data measured or the stability indicator 4 are preferably wholly or partially derived and integrated according to the relative humidity. In order to do this it is preferable if the grid lines, patterns or the like which correspond in particular to a defined storage time and which extend in the direction of the humidity axis are derived according to the relative humidity.

Preferably, and more particularly subsequently, derived values are once again obtained which in this case are associated with the relative humidity prevailing in the packaging at the respective measuring time. Integration of the data series according the relative humidity results in another partial integral $\int (\partial h / \partial (rh)) \, \delta rh$.

Preferably, particularly subsequently, the two partial integrals are added to the starting value of the active substance decomposition, which is ideally "zero", so as to obtain the following function: $h(t) = \int (\partial h(t, rh(t)) / \partial t) \, dt = \int (\partial h / \partial t) \, \delta t + \int (\delta h / \delta (rh)) \, \delta rh$. This function preferably represents a result of the SynPD simulation calculation, preferably describes the pattern of the decomposition, i.e. the product stability in this packaging candidate depending on the storage time under particular climatic conditions. The result is preferably part of the suitability indicator 1 or forms this indicator.

h or h(t) is or preferably corresponds to a degradation of the substance 3 or is or corresponds to the stability indicator 4 or a part thereof.

Derivation and integration according to the two influencing factors—relative humidity and/or storage time—is particularly advantageous when the product parameter being investigated is dependent both on the relative humidity and on the storage time. If only one particular stress factor were actually to trigger changes in the product, it might be sufficient to carry out the differential and integral calculations only for this one factor.

Preferably, the simulation results, viewed graphically, constitute a vertical projection, parallel projection and/or orthogonal projection of the time/humidity profile of the packaging onto the matrix surface or the hypersurface of the product properties.

If the product undergoes constantly increasing decomposition in the packaging, a pattern or development of the stability of the substance 3 is located particularly in the same plane as the hypersurface. In this way the behavior of the product under the given conditions can be simulated or calculated with the hypersurface.

The determination of the stability of the substance 3 in the packaged state using the packaging system 2 can be carried out graphically in the manner described, even if the graphs, areas or the like are not shown. Moreover, alternative procedures for determining the degree of decomposition of the substance 3 are also possible.

According to a curve pattern the proportion of the decomposed active substance increases to about 2% over the storage time if a final humidity of 10% r.h./25° C. is established in the packaging. If, by contrast, the starting humidity of roughly 45% r.h./25° C. is maintained in the packaging or even increases still further over the running time, the decomposition limit of 4% specified is reached or exceeded after only 18 months' storage.

The SynPD model curve calculated for an investigation parameter, in this case the decomposition of the active substance, is preferably tested with real packaging studies. For this purpose the product is stored and analyzed under the same conditions as were assumed in the calculation. In one example, the decomposition rate for a storage period of 18 months was calculated beforehand using the 6 months values available for permeation data.

Other aspects or steps of the present invention preferably comprise:
- identifying variables relevant to stability (e.g. decomposition, breaking force, disintegration, dissolution); and/or
- identifying the determining influencing parameters and optionally their interaction (e.g. humidity, temperature, time, light, covering visible and UV spectrum, oxygen concentration, solvent (alcohol) concentration); and/or
- measuring the effect of these parameters on the product individually and combined with one another (storage concept); and/or
- scientifically based on this, obtaining a fingerprint of the product properties relevant to stability (stability hypersurface which preferably forms the stability indicator 4 or part of it); and/or
- clearly calculating this mathematically/analytically with the development of the influencing parameters (e.g. breaking force with relative humidity in test packages over the storage time);
- being able to calculate beforehand the stability characteristics of the product under all the conditions incorporated in the design (e.g. breaking force in every possible packaging configuration, in all marketing packs, for all climates, during the storage period and in use), and in the event of subsequent changes in the parameters (type of packaging, desiccant, slight changes in the formulation) providing an existing database for further stability calculations very close together in time; and/or
- providing a generally applicable and hence efficient concept (quality by design approach which may be applied for example to decomposition, breaking force, dissolution, fine particle dose, sensitivity to light and oxygen, etc.); and/or
- for determining the stability indicator (4) and/or examining the stability of the substance (3), the storage temperature is less than 70° C., preferably less than 60° C., in particular less than 50° C.; and/or
- for determining the stability indicator (4) or examining the stability of the substance (3), the storage relative humidity applied to the substance or the relative humidity of the ambient condition (5) is less than 70% r.F., preferably less than 60% r.h., in particular less than 50° C.; and/or
- a (maximum) storage time for determining the stability indicator (4) preferably exceeds 1 month, further preferably 2 month, in particular 3 months or 6 months; and/or
- the stability of the substance (3) packaged with the packaging system (2) is simulated as or by means of the stability indicator (4); and/or
- the stability of the substance (3) packaged with the packaging system (2) is optimized by amendment of stability influencing factors, in particular by varying components or procedures the packaging system (2) is characterized by; and/or
- non-linear or non-linearized sorption isotherms or corresponding sorption data/sorption characteristics are approximated and/or used; and/or
- relaxation times, in particular with regard to humidity or water content of the packaging material and/or the substance, are considered, in particular for determining starting points; and/or
- a compatibility of the substance (3) with particular packaging material, preferably for determining the stability indicator (4), is examined by storing the substance (3) directly with parts or sections of the packaging material, preferably wherein a sample of the substance (3) stored with and a different sample (3) stored without the parts or sections of the packaging material are examined and the examination results are compared or considered differently; and/or
- a quantity of drying agent, in particular a drying agent preconditioned for a particular relative humidity, is determined or estimated, preferably by means of the (SynPD) model; and/or
- an arrangement and/or a position to each other and/or a number of multiple instances of the substance 3 to be packaged, e.g., tablets in a blister or a bottle, are considered for determining, in particular calculating or simulating, the suitability indicator 1 and/or the packaging system 2; and/or a particular packaging system 2, which can be considered or determined according to the present invention, comprises one or more drying processes and/or further preconditioning processes prior to the packaging process as such, in particular, the substance 3 and/or the packaging material is or are used pre-dried for packaging the substance 3; and/or a particular packaging system 2, which can be considered or determined according to the present invention, comprises; and/or a particular packaging system 2, which can be considered or determined according to the present invention, comprises a primary packaging enclosed in a secondary packaging, in particular a blister in a pouch or in a bottle, preferably wherein at least between the primary and the secondary package or packaging material a drying agent is placed; and/or the stability indicator 4 is, comprises and/or is visualizable as the hypersurface; and/or the stability indicator 4 comprises multiple stability indicator values 11 and/or an a assignment or function preferably defining stability indicator values 11, in particular a three-dimensional or multi-dimensional function, the stability indicator values 11 each and/or the function assigning or linking a) a particular ambient condition 5 or stability influencing factor, with b) a degradation (indicator, level, property), and with c) the (storage) time; and/or the suitability indicator 1 is determined or calculated by means of determining an assignment, linkage or function a) over (storage) time of b) a particular ambient condition 5 or stability influencing factor of the substance 3 packaged with the respective packaging system 2 and, preferably, by (parallel or orthogonal) projecting the assignment or function on the stability indicator 4; and/or for open storage at constant water content of the substance 3 (while solely varying the temperature or solely a different ambient condition 5), the relative humidity can be adapted such that the absolute water content of the substance 4 remains unchanged and/or that a humidity gradient becomes zero alternatively it is preferred that the substance 3 is
  enclosed such that any change in water content is avoided or minimized,
in particular by enclosing the substance 3 in an (diffusion tight/water tight/vapor tight/aluminum) package, preferably at least basically in direct contact with the substance 3 or avoiding enclosing any volume not filled with substance 3
in particular wherein the substance 3 is pre-conditioned, in particular with a particular water content/humidity, for example at a particular relative humidity and a particular temperature (e.g., room temperature, 25° C.)
the substance 3 can be packaged at least essentially without any volume not filled with substance 3 after pre-conditioning and storing the substance packaged in this manner at a temperature different than the pre-conditioning temperature (e.g., 40° C.), in particular such that the water content/absolute humidity is forced unvariable; and/or aspects of the present invention relating to water content, absolute humidity or relative humidity can generally be applied to volatile matter or volatile components of the substance (5)—thus the terms water content can be replaceable with content of volatile components and/or (relative) humidity with (relative) concentration of volatile components.

One advantage of the invention is that for the simulation of active substance breakdown and decomposition reactions and also for the release of active substance from the product, there is no need either to explicitly determine reaction mechanisms or reaction kinetics, or even to identify catalysis mechanisms. The above-mentioned processes are simulated with all their effects on the product in the open storage data. In addition, the SynPD modeling prevents trial and error loops at a later stage in the project which were previously put down to the experience-based choice of packaging means. Thus, using the controlled procedure, the period of time up until market launch can be reduced or optimized. In addition, the packaging stability can be obtained with a high probability of success, as the reaction of the product to various stress factors is well known thanks to the open storage data and only the most suitable packages are used in the stability study.

A number of embodiments, in addition to those discussed thus far are be characterized by the following numbered combinations of elements:

1. Method for calculating a suitability indicator (1), which corresponds to a suitability of a packaging system (2) for packaging a substance (3), preferably a development over time of the uptake of water by the substance (3) packed by means of the packaging system (2) and/or a development over time of a degradation of the substance (3) packed by means of the packaging system (2), wherein a stability indicator (4) which corresponds to a physical and/or chemical stability of the substance (3) or of a component of the substance (3) is determined as a function of at least one ambient condition (5) of the substance (3), preferably relative humidity and/or temperature of the environment or surrounding area of the substance (3), and wherein the suitability indicator (1) is calculated based on at least one parameter (6) relating to the ambient condition (5), and with the stability indicator (4) of the substance (3).

2. Method according to combination 1, characterized in that the suitability indicator (1) is calculated independently of the packaging system (2) and/or by storing the substance (3) in the unpackaged state, and/or that parameter (6) corresponds to a sorption characteristic/comprises sorption data (14) and/or corresponds to a permeation property/comprises permeation data (13) of the package V of the packaging system (2).

3. Method according to combination 1 or 2, characterized in that the ambient condition (5) of the substance (3) being packaged in the packaging system (2) is calculated.

4. Method according to combination 3, characterized in that the ambient condition (5) of the substance (3) packaged in the packaging system (2) is calculated with the at least one parameter (6) of the packaging system (2) relating to the ambient condition (5), and, preferably, the suitability indicator (1) is calculated with the ambient condition (5) that has been calculated.

5. Method according to one of combinations 2 to 4, characterized in that the parameters (6), preferably together with sorption characteristics or sorption data of the substance or parameters corresponding thereto, form a model (15), preferably a permeation model or a part thereof.

6. Method for calculating a suitability indicator (1), which corresponds to a suitability of a packaging system (2) for packaging a substance (3), preferably a development over time of the uptake of water by the substance (3) packed by means of the packaging system (2) and/or a development over time of a degradation of the substance (3) packed by means of the packaging system (2), particularly according to combination 1, wherein the suitability indicator (1) is calculated on the basis of a stability indicator (4) which corresponds to a physical and/or chemical stability of the substance (3) or of a component of the substance (3), on the basis of sorption characteristics of the substance (3) and on the basis of sorption data (14) and permeation data (13) of a package V or packaging material of the packaging system (2).

7. Method according to combination 6, characterized in that sorption characteristics of the substance (3) and sorption data (14) and permeation data (13) of package V or a packaging material of the packaging system (2) form a model, particularly a permeation model or a part thereof.

8. Method according to combination 5 or 7, characterized in that, using the model, ambient conditions (5) of the substance (3) packaged in the packaging system (2) are calculated.

9. Method according to combination 8, characterized in that using the ambient conditions (5) calculated for the substance (3) packaged in the packaging system (2), an influence on the substance (3), preferably a development over time, particularly of an uptake of water or of a water content of the substance (3), is or are calculated.

10. Method according to one of combinations 5 or 7 to 9, characterized in that the suitability indicator (1) is calculated using the model and/or the calculated influence of the calculated ambient conditions (5) on the substance (3), preferably based on the stability indicator (4).

11. Method according to one of combinations 2 to 10, characterized in that sorption characteristics and/or the stability indicator (4) of the substance (3) are determined independently of the sorption data (14) and permeation data (13) of the package V or packaging material of the packaging system (2); and/or in that sorption data (14) and permeation data (13) of the package V or packaging material of the packaging system (2) are determined independently of the sorption characteristics and/or the stability indicator (4) of the substance (3).

12. Method according to one of the preceding combinations, characterized in that the substance (3) is a medicament, the medicament preferably comprising as a component at least one active substance and/or an excipient and/or being present as a solid, preferably in the form of a number of discrete units, in the form of a loose dry compacted material, in the form of tablets or in the form of capsules.

13. Method according to one of the preceding combinations, characterized in that the stability indicator (4) is determined, preferably measured, on the basis of properties of the substance (3), after the substance (3) has been exposed, in an open or unpackaged state, to specific, preferably constant, ambient conditions (5) over a defined period of time.

14. Method according to one of the preceding combinations, characterized in that the stability indicator (4) comprises a plurality of stability indicator values (11) which preferably correspond to properties of the substance (3), particularly physical and/or chemical changes, after the substance (3) has been exposed, in an open or unpackaged state, to different ambient conditions (5), which are preferably constant for the particular stability indicator value (11), and/or over different, defined periods of time.

15. Method according to combination 14, characterized in that a group of stability indicator values (11) is determined, the group of stability indicator values (11) being determined by varying only the humidity of the environment or surrounding area of the substance (3) and/or the temperature while keeping the water content of the substance (3) constant and, preferably, stability indicator values (11) are determined for different periods of time over which the substance (3) has been exposed to the particular, preferably unchanging, ambient condition (5).

16. Method according to one of the preceding combinations, characterized in that the stability indicator (4) comprises stability indicator values (11) relating to a plurality of different ambient conditions (5) and in that the suitability indicator (1) is calculated with these stability indicator values (11) and with a plurality of parameters (6) of the packaging system (2) relating to the particular ambient conditions (5), the parameters (6) representing the behavior of the packaging system (2) in terms of different ambient conditions (5).

17. Method according to one of the preceding combinations, characterized in that the suitability indicator (1) represents or predicts a stability of the substance (3) when packaged using the packaging system (2), and/or in that the suitability indicator (1) is configured to enable the suitability of the packaging system (2) for the substance (3) to be evaluated.

18. Method according to one of the preceding combinations, characterized in that the suitability indicator (1) comprises a plurality of suitability indicator values which correspond to properties of the substance (3) or predict properties of the substance (3), after the substance (3), packaged using the packaging system (2), has been stored over different periods of time.

19. Method according to one of combinations 2 to 18, characterized in that the suitability indicator (1) is calculated by extrapolating or predicting the stability characteristics of the substance (3) when packaged using the packaging system (2), using the stability indicator (4) and one or a number of parameters (6) of the packaging system (2).

20. Method according to one of the preceding combinations, characterized in that the suitability indicator (1) and/or the stability indicator (4) corresponds to at least one degradation property or degradation tendency of the substance (3), preferably to a property or degradation tendency dependent on the ambient condition (5).

21. Method according to one of the preceding combinations, characterized in that the suitability indicator (1) and/or the stability indicator (4) corresponds to a chemical stability of the substance (3) or of a component of the substance (3), particularly to a dissolution or decomposition, and/or to the mechanical stability of the presentation form of the substance (3), particularly its breaking force or disintegration, and/or to the stability of the distribution of different ingredients in the substance (3).

22. Method according to one of the preceding combinations, characterized in that die ambient condition (5) is or comprises a humidity, preferably a, particularly relative, humidity, and/or a temperature, particularly ambient temperature, preferably in direct contact with the substance (3).

23. Method according to one of the preceding combinations, characterized in that the following is or are also taken into account when calculating the suitability indicator (1) and/or in the simulation model:

a water content or a relative humidity of an atmosphere which is found or is to be enclosed within the package (V) in the packaging process using the packaging system (2), and which is in direct content with this substance (3) when it is packaged in the packaging system (2), and/or a water content or a relative humidity of the packaging material; and/or a water content or a relative humidity of the substance (3), the water content or the relative humidity being used particularly to calculate the suitability indicator (1), to determine the packaging system (2), to calculate the ambient conditions (5) in the packaged state of the substance (3), any influence of the ambient conditions (5) on the substance (3) and/or the stability of the substance (3) packaged in the packaging system (2).

24. Method for selecting and/or automatically determining one or more packaging systems (2) for a substance (3), particularly a medicament, wherein, using a model (15) having at least permeation data (14) and sorption data (13) of a package (V) or one or more packaging materials of the packaging system (2) and sorption characteristics of the substance (3), a packaging system (2) is determined or selected and/or a suitability indicator (1), particularly according to one of the preceding combinations, is calculated, which corresponds to the suitability of the respective packaging system (2) for packaging the substance (3) using the packaging system (2), particularly under defined climatic ambient conditions (5); and/or wherein a suitability indicator (1) is calculated for at least two different packaging systems (2) using the method according to one of the preceding combinations, the suitability indicators (1) are compared with one another and/or with at least one target value and, preferably, one or more packaging systems (2) is or are automatically selected or discarded using the results of the comparison and/or a better suitability of one packaging system (2) compared with another packaging system (2) is indicated, signaled and/or displayed.

25. Method according to combination 24, characterized in that a combination of packaging material or packaging materials and the geometric shape of the packaging material (s) forming the package (V) is selected or determined, preferably so that the combination is suitable for packaging the substance (3) and enables subsequent storage to take place under certain climatic conditions over a given period of time without any degradation of the substance (3) exceeding a certain threshold when stored under these conditions in the packaged state.

26. Method according to combination 24 or 25, characterized in that a plurality of theoretically suitable packaging systems (2) are selected or determined and the properties and/or suitability indicators (1) that characterize the packaging systems (2) are displayed as a comparison or contrasting juxtaposition.

27. Method according to one of the preceding combinations, characterized in that the packaging system (2) and/or the package V is or are characterized at least by the chemical composition of one or more packaging materials and by a geometric shape of the packaging material or materials and, preferably, also by process conditions of the packaging process or its effects on the substance (3) and/or the packaging materials and/or by the atmosphere enclosed together with the substance (3) during the packaging process.

28. Method according to one of the preceding combinations, characterized in that the package (V) and/or the packaging material is characterized by its chemical composition and a geometric shape, while preferably sorption data (14) and permeation data (13) of the package (V) or packaging material take account of both the chemical composition and the geometric shape.

29. Method according to one of the preceding combinations, characterized in that sorption data (14) and/or sorption characteristics comprise, or are represented by, sorption isotherms or sorption capacities; and/or in that permeation data (13) comprise, or are represented by, a permeability or permeation rate, particularly in respect of water.

30. System (S) for calculating a suitability indicator (1) which corresponds to a suitability of a packaging system (2) for packaging a substance (3), and/or for selecting and/or automatically determining one or more packaging systems (2), the system being configured to carry out a method according to one of the preceding combinations.

31. System according to combination 30, characterized in that the system (S) comprises an input device for inputting a stability indicator (4) of a substance (3) as a function of at least one ambient condition (5), particularly a measuring device (9), and a calculating device, in particular Link (7), for calculating the suitability indicator (1) with at least one parameter (6) of the packaging system (2) relating to the ambient condition (5) and with the stability indicator (4) of the substance (3); and/or in that the system (S) comprises a packaging system database (12) in which at least one, preferably a plurality, of parameters (6) being specific to one or more packages (V) or packaging systems (2) is or are stored, preferably wherein the calculating device or link (7) is configured to calculate a suitability indicator (1) with the parameter (6) and/or the stability indicator (4).

32. Method for determining a stability indicator (4) which corresponds to a physical and/or chemical stability of a substance (3) or of a component of the substance (3), wherein the physical and/or chemical stability depends on multiple stability influencing factors and/or ambient conditions (5), wherein the stability indicator (3) is determined depending on one particular of the stability influencing factors and/or ambient conditions (5) while further or the remaining stability influencing factors and/or ambient conditions (5) are kept unvaried, in particular wherein the stability influencing factors and/or ambient conditions (5) comprise a relative humidity of the ambient or atmosphere being in direct contact with the substance (3), and/or an absolute water content of the substance (3), and/or the temperature of the substance (3).

33. Method according to combination 32, characterized in that the stability indicator (4) is a function and is determined depending on time, preferably, thus the stability indicator (4) indicating a physical and/or chemical stability of the substance (3) or of a component of the substance (3) as a function of both time and the particular one of the stability influencing factors, in particular wherein the function is expressed, expressable, interpolated and/or interpolable as a hypersurface.

34. Method according to combination 32 or 33, characterized in that the stability indicator (4) for a particular point in time and/or a suitability indicator (1) is calculated by means of determining a progress or function of the particular stability influencing factor or ambient condition (5) over time and projecting the progress or function to or substituting it in the stability indicator (4), preferably projecting it to a hypersurface comprised of or formed by or usable to visualize the suitability indicator (1), further preferably using or generating an orthographic projection or parallel projection, in particular in the direction of degradation and/or wherein the stability indicator (4) and/or the hypersurface is or are defined in an at least three dimensional system comprising one or more ambient condition (5), a degradation or corresponding indicator, and a time, in particular storage time, or comprises respective information.

35. Method according to any one of combinations 32 to 34, characterized in that an influence on the substance (3) of the ambient conditions (5) relative humidity of atmosphere being in direct contact with the substance (3) and temperature are determined independently of one another, preferably by storing the substance (3) at varying relative humidity while keeping the temperature unvarying and/or by storing the substance (3) at varying the temperature while keeping the absolute water content of the substance (3) unvarying, 36. Method for determining a packaging system (2), the packaging system (2) comprising a package (V) or at least one or more packaging materials for packaging a substance (3), wherein
  A) a permeation behavior of the packaging material in a particular shape for packaging the substance (3), in particular a deep drawn shape, is determined and/or considered; and/or
  B) sorption data (14) and/or a water content of the packaging material is or are considered, preferably in addition to sorption characteristics and water content of the substance (3); and/or
  C) a suitability indicator (1) according to any one of combinations 1 to 29 is determined and/or considered; and/or
  D) a stability indicator (3) according to any of combinations 32 to 35 is determined and/or considered; and/or
  E) a water content and/or relative humidity at least of the packaging material, and of the substance (3) is or are considered; and/or
  F) a chemical structure of the packaging material, and/or geometrical properties of the packaging material, and/or preconditioning requirements for the packaging material, and/or preconditioning requirements for the substance, and/or an amount of drying agents to be placed inside the package (V) together with the substance (3), and/or an amount of auxiliary materials being part of substance (3) or which is to be placed inside the package (V) together with the substance (3) is or are considered and/or determined, preferably calculated based on a model (15) and/or with a simulation environment, automatically, and/or iteratively.

37. Simulation environment for determining a packaging system (2) for packaging a substance (3) and/or for determining a suitability of the packaging system (2) to achieve a preset stability of the substance (3) when packaged with the packaging system (2), in particular represented by a stability indicator (4), characterized in that the simulation environment is configured to carry out the steps of any one of combinations 1 to 29 and 32 to 37.

38. Method for determining a stability indicator (4) which corresponds to a physical and/or chemical stability of the substance (3) or of a component of the substance (3), wherein a set of multiple samples of the substance (3) are examined at the same time under different ambient conditions (5) characterized in that a particular one or more of the samples of the substance (3) is or are exposed to conditions where a minimum stability of the samples of the sample set can be expected, in particular a maximum temperature and/or relative humidity within the sample set, and that one or one of the particular one or more samples is examined at several subsequent time-points until a stability degradation of the particular one or more samples is determined and only after this determination, one or more of the further samples of the set are examined as well.

39. Method according to combination 38, varying only one particular stability influencing factor or ambient condition (5) per sample and keeping further and/or the remaining stability influencing factors or ambient conditions (5) unvarying.

40. Computer-readable storage medium or computer program product comprising program code means which when executed are configured to carry out the steps of the method according to one of combinations 1 to 29, 32 to 36, 38 and 39.

| List of reference numerals: | |
|---|---|
| 1 | Suitability indicator |
| 2 | Packaging system |
| 3 | Substrate |
| 4 | Stability indicator |
| 5 | Ambient condition |
| 6 | Parameter |
| 7 | Link |
| 8 | Climate control device |
| 9 | Measuring device |
| 10 | Database |
| 11 | Stability indicator value |
| 12 | Packaging system database |
| 13 | Permeation data |
| 14 | Sorption data |
| 15 | Overall model/SynPD model |
| 16 | Receptacle |
| 17 | Volume-forming device |
| 18 | Closure means |
| S | System |
| T | Arrow |
| V | Package |

The invention claimed is:

1. A method, comprising:
  computing by simulation a respective suitability indicator for each of a plurality of packaging systems, where each such packaging system is a candidate for packaging a substance, wherein each suitability indicator corresponds to a respective suitability of a respective one of the plurality of packaging systems to protect the substance under defined climatic ambient conditions, wherein the suitability indicator is computed based on: (i) a stability indicator, which corresponds to at least one of a physical and chemical stability of the substance, or of a component of the substance, and which is determined as a function of at least one ambient condition of the substance, and (ii) a permeation model, which includes: (a) sorption data of the substance or parameters corresponding thereto, (b) at least one of the sorption data of the package, permeation data of the package and the at least one parameter relating to the at least one ambient condition of the substance; and
  selecting one or more of the plurality of packaging systems based on the suitability indicator.

2. The method according to claim 1, wherein the at least one ambient condition is a relative humidity or temperature of the surrounding area of the substance, the surrounding area being in direct contact with the substance.

3. The method according to claim 1, wherein the ambient condition is computed with at least one parameter relating to the ambient condition, and each of the respective suitability indicators is calculated with the ambient condition that has been computed.

4. The method according to claim 1, wherein each of the respective suitability indicators corresponds to a development over time of the uptake of water by the substance, or a development over time of a degradation of the substance or a component of the substance, disposed within a corresponding one of the packaging systems.

5. The method according to claim 1, wherein each of the respective suitability indicators represents or predicts a stability of the substance when packaged within a corresponding one of the packaging systems.

6. The method according to claim 1, wherein a development over time of an uptake of water, or of a water content, of the substance are computed using the permeation model, using said ambient conditions of the substance.

7. The method according to claim 1, wherein at least one of:
the stability indicator of the substance is determined independently of the sorption data of the plurality of packages, and
sorption data of the plurality of packages are determined independently of the stability indicator of the substance.

8. The method according to claim 1, wherein the substance is being present as a solid in the form of a number of discrete units, in the form of a loose dry compacted material, in the form of tablets or in the form of capsules.

9. The method according to claim 1, wherein the stability indicator is determined on the basis of properties of the substance after the substance has been exposed, in an open or unpackaged state, to constant ambient conditions over a defined period of time.

10. The method according to claim 1, wherein the stability indicator comprises a plurality of stability indicator values which correspond to properties of the substance after the substance has been exposed, in an open or unpackaged state, to different ambient conditions, which are constant for the particular stability indicator value over different, defined periods of time.

11. The method according to claim 9, wherein a group of stability indicator values is determined, the group of stability indicator values being determined particular ambient conditions according to at least one of:
by varying only the relative humidity of the surrounding area of the substance, and
by varying only the temperature,
while keeping the water content of the substance constant, and stability indicator values are determined for different periods of time over which the substance has been exposed to the particular ambient condition.

12. The method according to claim 9, wherein the suitability indicator is computed with these stability indicator values and with a plurality of parameters of the plurality of packaging systems relating to the particular ambient conditions, the parameters representing the behavior of the plurality of packaging systems in terms of different ambient conditions.

13. The method according to claim 1, wherein the suitability indicator comprises a plurality of suitability indicator values which correspond to properties of the substance or predict properties of the substance, after the substance, packaged using one of the plurality of packaging systems, has been stored over different periods of time.

14. The method according to claim 1, wherein the suitability indicator is computed by extrapolating or predicting the stability characteristics of the substance when packaged using one of the plurality of packaging systems, using the stability indicator and one or a number of parameters of the plurality of packaging systems.

15. The method according claim 1, wherein at least one of the following is also taken into account when computing the suitability indicator:
a water content or a relative humidity of an atmosphere which is found or is to be enclosed within the package in the packaging process using the plurality of packaging systems, and which is in direct contact with this substance when it is packaged in the plurality of packaging systems,
a water content or a relative humidity of the packaging material,
a water content or a relative humidity of the substance.

16. The method of claim 1, wherein:
the permeation model includes: permeation data of a package or one or more packaging materials of the plurality of packaging systems, sorption data of the package or one or more packaging materials of the plurality of packaging systems, and sorption data of the substance, and
at least two different ones of the plurality of packaging systems are evaluated by comparing at least two of the respective suitability indicators with one another and with at least one target value, and the one or more packaging systems is or are automatically selected or discarded using the results of the comparison or a better suitability of one packaging system compared with another packaging system is indicated, signaled or displayed.

17. The method according to claim 16, wherein a combination of packaging material or packaging materials and the geometric shape of the packaging material(s) forming the package is selected or determined, so that the combination is suitable for packaging the substance and enables subsequent storage to take place under certain climatic conditions over a given period of time without any degradation of the substance exceeding a certain threshold when stored under these conditions in the packaged state.

18. The method according to claim 1, wherein the package is characterized at least by the chemical composition of one or more packaging materials and by a geometric shape of the packaging material or materials and also by process conditions of the packaging process or its effects on at least one of the substance, the packaging materials and the atmosphere enclosed together with the substance during the packaging process.

19. The method according to claim 1, wherein the package is characterized by its chemical composition and a geometric shape, while sorption data and permeation data of the package take account of both the chemical composition and the geometric shape.

20. The method of claim 1, wherein each stability indicator is determined depending on only one particular stability influencing factors or ambient conditions, among a plurality of such stability influencing factors or ambient conditions, while further or the remaining stability influencing factors or ambient conditions are kept unvaried.

21. The method according to claim 20, wherein the stability influencing factors or ambient conditions comprise at least one of a relative humidity of the ambient or atmosphere being in direct contact with the substance, an absolute water content of the substance, and the temperature of the substance.

22. The method according to claim 20, wherein each stability indicator is a function and is determined depending on time, such stability indicator indicating at least one of a physical and chemical stability of the substance or of a component of the substance as a function of both time and the particular one of the stability influencing factors, and wherein the function is expressable or interpolable as a hypersurface.

23. The method of claim 1, wherein a set of multiple samples of the substance are examined at the same time under different ambient conditions, wherein a particular one or more of the samples of the substance is or are exposed to conditions where a minimum stability of the samples of the sample set can be expected, and wherein one or one of the particular one or more samples is examined at several subsequent time-points until a stability degradation of the particular one or more samples is determined and only after this determination, one or more of the further samples of the set are examined as well.

* * * * *